United States Patent
Pan et al.

(10) Patent No.: US 12,234,267 B2
(45) Date of Patent: Feb. 25, 2025

(54) IDENTIFICATION OF MUTATIONS IN CHANNELOPSIN VARIANTS HAVING IMPROVED LIGHT SENSITIVITY AND METHODS OF USE THEREOF

(71) Applicant: Wayne State University, Detroit, MI (US)

(72) Inventors: Zhuo-Hua Pan, Troy, MI (US); Tushar Ganjawala, Canton, MA (US); Qi Lu, Detroit, MI (US); Gary Abrams, Detroit, MI (US)

(73) Assignee: Wayne State University, Detroit, MI (US)

( * ) Notice: Subject to any disclaimer, the term of this patent is extended or adjusted under 35 U.S.C. 154(b) by 627 days.

(21) Appl. No.: 17/324,501

(22) Filed: May 19, 2021

(65) Prior Publication Data

US 2022/0089660 A1 Mar. 24, 2022

Related U.S. Application Data

(62) Division of application No. 16/328,916, filed as application No. PCT/US2017/049158 on Aug. 29, 2017, now Pat. No. 11,041,004.

(60) Provisional application No. 62/380,871, filed on Aug. 29, 2016.

(51) Int. Cl.
*C07K 14/405* (2006.01)
*A61K 35/00* (2006.01)
*A61K 38/00* (2006.01)
*A61P 27/02* (2006.01)

(52) U.S. Cl.
CPC ............ *C07K 14/405* (2013.01); *A61P 27/02* (2018.01); *A61K 35/00* (2013.01); *A61K 38/00* (2013.01)

(58) Field of Classification Search
None
See application file for complete search history.

(56) References Cited

U.S. PATENT DOCUMENTS

| | | |
|---|---|---|
| 8,470,790 B2 | 6/2013 | Pan et al. |
| 9,193,956 B2 | 11/2015 | Schaffer |
| 10,392,426 B2 | 8/2019 | Klapoetke |
| 11,041,004 B2 | 6/2021 | Pan |
| 11,324,824 B2 | 5/2022 | Shemesh |
| 2010/0008170 A1 | 1/2010 | Sato et al. |
| 2015/0223679 A1 | 8/2015 | Klapoetke et al. |
| 2016/0346359 A1 | 12/2016 | Buchlis |

FOREIGN PATENT DOCUMENTS

| | | |
|---|---|---|
| EP | 2614079 B1 | 3/2012 |
| JP | 2016519063 A | 6/2016 |
| RU | 2595384 C2 | 8/2016 |
| WO | 9522618 A1 | 8/1995 |
| WO | 2007024391 A2 | 3/2007 |
| WO | 2007131180 A2 | 11/2007 |
| WO | 2011140279 A1 | 11/2011 |
| WO | 2013071231 A1 | 5/2013 |
| WO | 2013134295 A1 | 9/2013 |
| WO | 2014160281 A2 | 10/2014 |
| WO | 2015138616 A1 | 9/2015 |
| WO | 2015161308 A1 | 10/2015 |
| WO | 2017173283 A1 | 10/2017 |
| WO | 2017210664 A1 | 12/2017 |
| WO | 2018022905 A2 | 2/2018 |
| WO | 2018044912 A1 | 3/2018 |

OTHER PUBLICATIONS

Healthline (downloaded from URL :<https://www.healthline.com/health/eye-health/granulomatous-conjunctivitis>) (Year: 2024).*
National Eye Institute (downloaded from URL: <https://www.nei.nih.gov/learn-about-eye-health/eye-conditions-and-diseases/stargardt-disease#:~:text=Vision%20loss%20usually%20starts%20in,most%20of%20their%20remaining%20vision>) (Year: 2024).*
Ning Ding et al., Electrophysiological Properties of Voltage-gated Potassium Channels of Cultured Newborn Bovine Retinal Neurons, Apr. 30, 2007, Journal of Capital Medical University, vol. 28, issue 2, p. 239-242.
International Search Report and Written Opinion corresponding to International Patent Application No. PCT/US17/49158, mailed on Nov. 7, 2017, 10 pages.
Arnau et al. (Jul. 2006) "Current Strategies for the Use of Affinity Tags and Tag Removal for the Purification of Recombinant Proteins", Protein expression and purification, 48(1):1-13.
Berndt et al. (May 3, 2011) "High-efficiency Channelrhodopsins for Fast Neuronal Stimulation at Low Light Levels", Proceedings of the National Academy of Sciences, 108(18):7595-7600.
Berry et al. (Oct. 1992) "Substitution of Cysteine for Selenocysteine in Type I Iodothyronine Deiodinase Reduces the Catalytic Efficiency of the Protein but Enhances its Translation", Endocrinology, 131(4):1848-1852.
Bi et al. (Apr. 6, 2006) "Ectopic Expression of a Microbial-Type Rhodopsin Restores Visual Responses in Mice with Photoreceptor Degeneration", Neuron, 50(1):23-33.
Frankel et al. (Aug. 2000) "Characterization of Diphtheria Fusion Proteins Targeted to the Human Interleukin-3 Receptor", Protein Eng., 13(8):575-581.
Gasser et al. (2007) "Antibody Production with Yeasts and Filamentous Fungi: On the Road to Large Scale?", Biotechnology Letters, 29(2):201-212.

(Continued)

*Primary Examiner* — Sergio Coffa
(74) *Attorney, Agent, or Firm* — KDW FIRM PLLC

(57) ABSTRACT

The invention provides compositions and kits including at least one nucleic acid or polypeptide molecule encoding for a mutant CoChop protein. Methods of the invention include administering a composition comprising a mutant CoChop to a subject to preserve, improve, or restore phototransduction. Preferably, the compositions and methods of the invention are provided to a subject having impaired vision, thereby restoring vision to normal levels.

11 Claims, 10 Drawing Sheets

Specification includes a Sequence Listing.

(56) References Cited

OTHER PUBLICATIONS

Kaplitt et al. (Oct. 1994) "Long-Term Gene Expression and Phenotypic Correction Using Adeno-Associated Virus Vectors in the Mammalian Brain", Nature Genetics, 8(2):148-154.
Klapoetke et al. (Feb. 9, 2014) "Independent Optical Excitation of Distinct Neural Populations", Nature Methods, 11(3):28 pages.
Kleinlogel et al. (Mar. 13, 2011) "Ultra Light-sensitive and Fast Neuronal Activation with the $Ca^{2+}$-permeable Channelrhodopsin CatCh", Nature Neuroscience, 14(4):28 Pages.
Muller et al. (Dec. 2008) "Spliceosomal Peptide P140 for Immunotherapy of Systemic Lupus Erythematosus: Results of an Early Phase II Clinical Trial", Arthritis & Rheumatism, 58(12):3873-3883.
Nagel et al. (Nov. 25, 2003) "Channelrhodopsin-2, a Directly Light-Gated Cation-Selective Membrane Channel", PNAS, 100(24):13940-13945.
Pakula et al. (1989) "Genetic Analysis of Protein Stability and Function", Anna. Rev. Genet., 23:289-310.
Pan et al. (Jun. 5, 2014) "ChR2 Mutants at L132 and T159 with Improved Operational Light Sensitivity for Vision Restoration", PloS One, 9(6):12 pages.
Pan et al. (2015) "Optogenetic Approaches to Restoring Vision", Annual Review of Vision Science, 1:185-210.
Powell et al. (Jan. 2015) "Viral Expression Cassette Elements to Enhance Transgene Target Specificity and Expression in Gene Therapy", Discovery Medicine, 19(102):15 Pages.
Singer et al. (1998) "Genes and Genomes: in 2 volumes", 1: 5 pages.
Tokuriki et al. (2009) "Stability Effects of Mutations and Protein Evolvability", Current Opinion in Structural Biology, 19:596-604.
Tomita et al. (Aug. 2007) "Restoration of Visual Response in Aged Dystrophic RCS Rats Using AAV-Mediated Channelopsin-2 Gene Transfer", Investigative Ophthalmology & Visual Science, 48(8): 3821-3826.
Wang et al. (Feb. 27, 2009) "Molecular Determinants Differentiating Photocurrent Properties of Two Channelrhodopsins from Chlamydomonas", Journal of Biological Chemistry, 284(9): 5685-5696 (14 pages).
Yang et al. (Jul. 1994) "High-level Expression and Deletion Mutagenesis of Human Tryptophan Hydroxylase", Proc Natl Acad Sci USA, 91(14):6659-6663.
Balkema GW et al., "Visually evoked eye movements in mouse mutants and inbred strains. A screening report." 1984, Invest Opthalmol Vis Sci. 25:795-800.
Davidson et al., "A model system for in vivo gene transfer into the central nervous system using an adenoviral vector" Nat. Genet, 3:219 (1993).
Hayes, JK et al., "Elevated dark-adapted thresholds in hypopigmented mice measured with a water maze screening apparatus" 1993, Behav Genet 23:395-403.
Hu and Pathak, "Design of Retroviral Vectors and Helper Cells for Gene Therapy" Pharmacol. Rev. 52:493-511, 2000.
La Salle et al., "An Adenovirus Vector for Gene Transfer into Neurons and Glia in the Brain" Science, 259:988 (1993).
Sakagami, K et al. "Physiology of rat retinal pericytes: modulation of ion channel activity by serum-derived molecules." The Journal of physiology vol. 521 Pt 3, Pt 3 (1999): 637-50. doi:10.1111/j.1469-7793.1999.00637.x.
Zheng et al., "Genomic integration and gene expression by a modified adenoviral vector" Nature Biotechnol. 18:176-186, 2000.
Dalkara et al., "In Vivo-Directed Evolution of a New Adeno-Associated Virus for Therapeutic Outer Retinal Gene Delivery from the Vitreous," Science Translational Medicine, vol. 5, Issue 189: 13 pages (Jun. 2013).
Lin et al., "ReaChR: A red-shifted variant of channelrhodopsin enables deep transcranial optogenetic excitation," Nature Neuroscience, vol. 16, No. 10: 1499-1508 (Oct. 2013) <doi: 10.1038/nn. 3502 >.
Naso et al., "Adeno-Associated Virus (AAV) as a Vector for Gene Therapy," BioDrugs, vol. 31: 317-334 (2017) <doi: 10.1007/s40259-017-0234-5 >.
Petit et al., "Advances in Gene Therapy for Diseases of the Eye," Human Gene Therapy, vol. 27, No. 00: 14 pages (2016) <doi: 10.1089/hum.20.16.040 >.
Prigge et al., "Color-tuned Channelrhodopsins for Multiwavelength Optogenetics," The Journal of Biological Chemistry, vol. 287, No. 38: 31804-31812 (Sep. 2012) <doi: 10.1074/jbc.M112.391185 >.
Russell, et al., "Efficacy and safety of voretigene neparvovec (AAV2-hRPE65v2) in patients with RPE65-mediated inherited retinal dystrophy: a randomised, controlled, open-label, phase 3 trial," Lancet, vol. 390(10097): 849-860 (Aug. 2017) <doi: 10.1016/S0140-6736(17)31868-8 >.
Terakita, "The Opsins," Genome Biology, vol. 6, Issue 3, Article 213: 213.1-213.9 (Mar. 2005).
Office Action in U.S. Appl. No. 16/328,916, dated Jan. 30, 2020, 15 pages.
Office Action in U.S. Appl. No. 16/328,916, dated Aug. 5, 2020, 7 pages.
Notice of Allowance issued in U.S. Appl. No. 16/328,916, dated Feb. 16, 2021, 5 pages.

\* cited by examiner

IDENTIFICATION OF MUTATIONS IN CHANNELOPSIN VARIANTS HAVING IMPROVED LIGHT SENSITIVITY AND METHODS OF USE THEREOF

RELATED APPLICATIONS

This application is a divisional application of U.S. patent application Ser. No. 16/328,916 filed Feb. 27, 2019, now U.S. Pat. No. 11,041,004 issued on Jun. 22, 2021, which is a national stage application, filed under 35 U.S.C. § 371, of PCT International Patent Application No. PCT/US2017/049158, filed on Aug. 29, 2017, and claims benefit of priority to U.S. Provisional Patent Application No. 62/380,871 filed on Aug. 29, 2016, both of which, including their contents, are incorporated herein by reference in their entireties.

STATEMENT OF GOVERNMENT SUPPORT

Part of the work performed during development of this invention utilized U.S. Government funds under the National Institutes of Health/National Eye Institute grant NIH EY 17130. The Government has certain rights in the invention.

DESCRIPTION OF THE TEXT FILE SUBMITTED ELECTRONICALLY

This application contains a Sequence Listing file entitled 052522-510D01US_ST25.txt, with a file size of about 24.75 kilobytes and created on or about 18 May 2021, has been submitted electronically in ASCII format and is hereby incorporated by reference in its entirety.

FIELD OF THE INVENTION

This invention relates generally to the field of molecular biology. Mutations in the Channelopsin variant gene (Co-Chop) are identified. Compositions comprising a mutant CoChop gene are used in therapeutic methods. For example, compositions comprising a mutant CoChop gene improve and restore vision loss.

BACKGROUND OF THE INVENTION

The retina is composed of photoreceptors (or photoreceptor cells, rods and cones). Photoreceptors are highly specialized neurons that are responsible for phototransduction, or the conversion of light (in the form of electromagnetic radiation) into electrical and chemical signals that propagate a cascade of events within the visual system, ultimately generating a representation of our world.

Photoreceptor loss or degeneration severely compromises, if not completely inhibits, phototransduction of visual information within the retina. Loss of photoreceptor cells and/or loss of a photoreceptor cell function are the primary causes of diminished visual acuity, diminished light sensitivity, and blindness. There is a long-felt need in the art for compositions and method that restore photosensitivity of the retina of a subject experiencing vision loss.

SUMMARY OF THE INVENTION

The invention provides an isolated light-activated ion channel polypeptide having the amino acid sequence of SEQ ID NO:2 and one or more amino acid modifications. An advantage of the CoChR mutants (e.g. mutant CoChop) disclosed herein is that these mutant polypeptides require less light than wild type CoChR (SEQ ID NO: 2) for activation. Thus, at the same light intensity, a greater level of ion flux and/or proton flux is observed in the mutant CoChR polypeptides than in the wild type. In some embodiments, the light-activated ion channel polypeptide has a least one of a greater level of an ion flux and a greater level of proton flux compared to the light-activated ion channel polypeptide of SEQ ID NO:2 when expressed in a cell membrane and contacted with activating light (e.g. above the threshold for activation). The light activated ion channel polypeptide has the amino acid sequence of any of one of SEQ ID NOs: 3-10. Optionally, the polypeptide further includes one or more amino acid modifications such as a substitution, deletion or insertion.

In another aspect the invention provides an isolated nucleic acid molecule that encodes for the polypeptide of the invention. Optionally the nucleic acid sequence is operably linked to a promoter sequence. Also included in the invention are vectors containing the nucleic acids according to the invention.

Also included in the invention is a cell containing the polypeptide or the nucleic acids according to the invention. The cell is for example a photoreceptor, a bipolar cell, a rod bipolar cell, an ON-type cone bipolar cell, a retinal ganglion cell, a photosensitive retinal ganglion cell, a horizontal cell, an amacrine cell, or an AII amacrine cell. The cell is in vitro, ex vivo or in vivo.

In other aspects the invention provides a method of changing the conductivity of a membrane by expressing in a host membrane the polypeptide of the invention and contacting the polypeptide with a light under suitable conditions to change the conductivity of the host membrane. The host membrane is a cell membrane such as a cell membrane of a neuronal cell, a nervous system cell, a cardiac cell, a circulatory cell, a visual system cell, or an auditory system cell.

In a further aspect the invention provides methods of treating a disease or condition in a subject comprising administering to a subject in need thereof a therapeutically effective amount of a nucleic acid or polypeptide according to the invention. The disease or condition is for example, injury, brain damage, spinal cord injury, epilepsy, a metabolic disorder, a cardiac dysfunction, vison loss, blindness, deafness, hearing loss or neurological condition.

In yet another aspect the invention features a method of improving or restoring vision, by administering to a subject a nucleic acid or polypeptide according to the invention. The subject is suffering from an ocular disease such as macular degeneration or retinitis pigmentosa.

Improving or restoring vision includes for example increasing light sensitivity; lowering the threshold light intensity required to elicit a photocurrent; increasing visual evoked potential in the visual cortex; and lowering the threshold light intensity to elicit visually guided behavior, such as optomotor responses.

In a further aspect the invention provides methods of treating retinitis pigmentosa or age related macular degeneration comprising administering to a subject in need thereof a nucleic acid or polypeptide according to the invention. The composition is administered by intravitreal or subretinal injection.

Other features and advantages of the invention will be apparent from and are encompassed by the following detailed description and claims.

DETAILED DESCRIPTION

Figure 1:
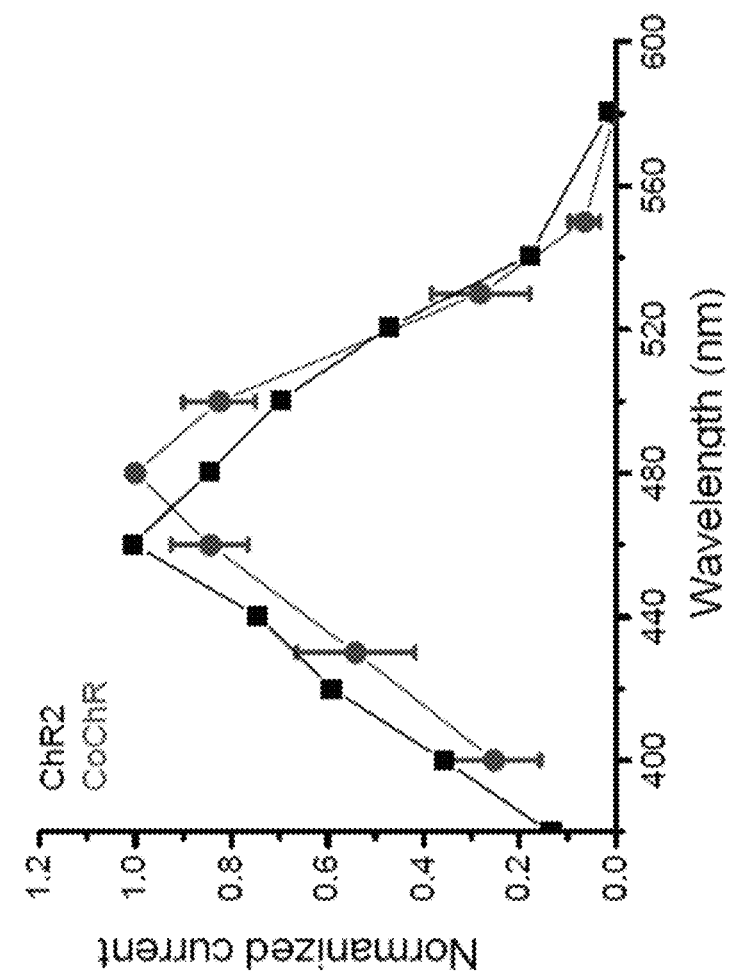
FIG. 1: Comparison of the spectral curves of CoChR and ChR2 in HEK cell recordings. The peak spectrum of CoChR is ~480 nm, which is slightly more red-shifted than that of ChR2.
Figure 2:
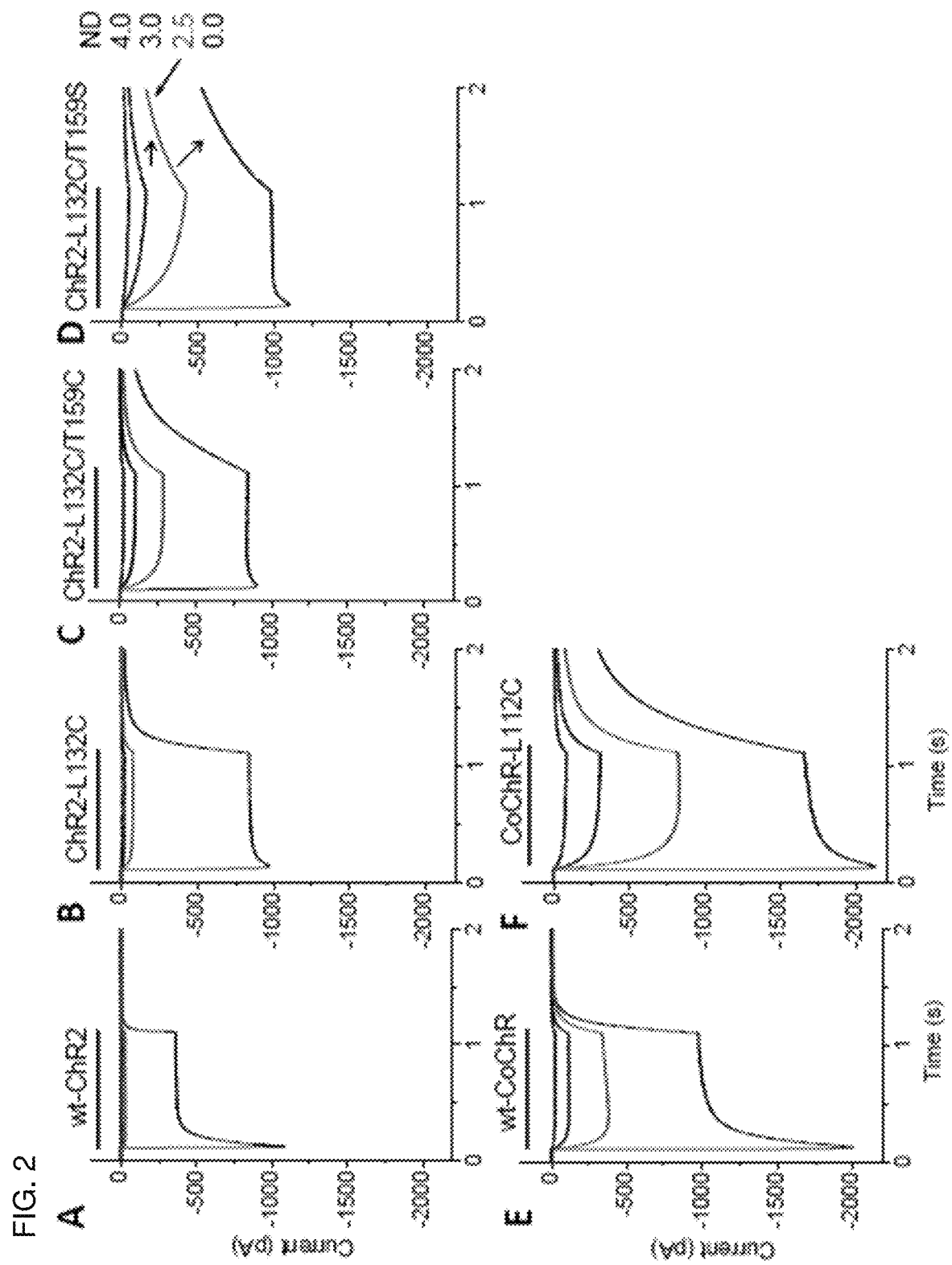
FIG. 2: Sample recordings of light evoked currents of CoChRs and ChR2s in HEK cell recordings. A-D, Light-evoked currents of wt-ChR2 (A), and its three mutants, ChR2-L132C (B), ChR2-L132C/T159C (C), and ChR2-L132C/T159C (D). The currents were evoked by incremental light intensities with neutral density (ND) filters at ND=0, 2.5, 3.0, and 4.0. The red traces were elicited by light at 460 nm with 2.5 neutral density (ND) ($4.1 \times 10^{15}$ photons/cm$^2$s). E and F, Light-evoked currents of wt-CoChR (E), and its mutant, CoChR-L112C (F). The red traces were elicited by light at 480 nm with 2.5 neutral density (ND) ($4.8 \times 10^{15}$ photons/cm$^2$s).
Figure 3:
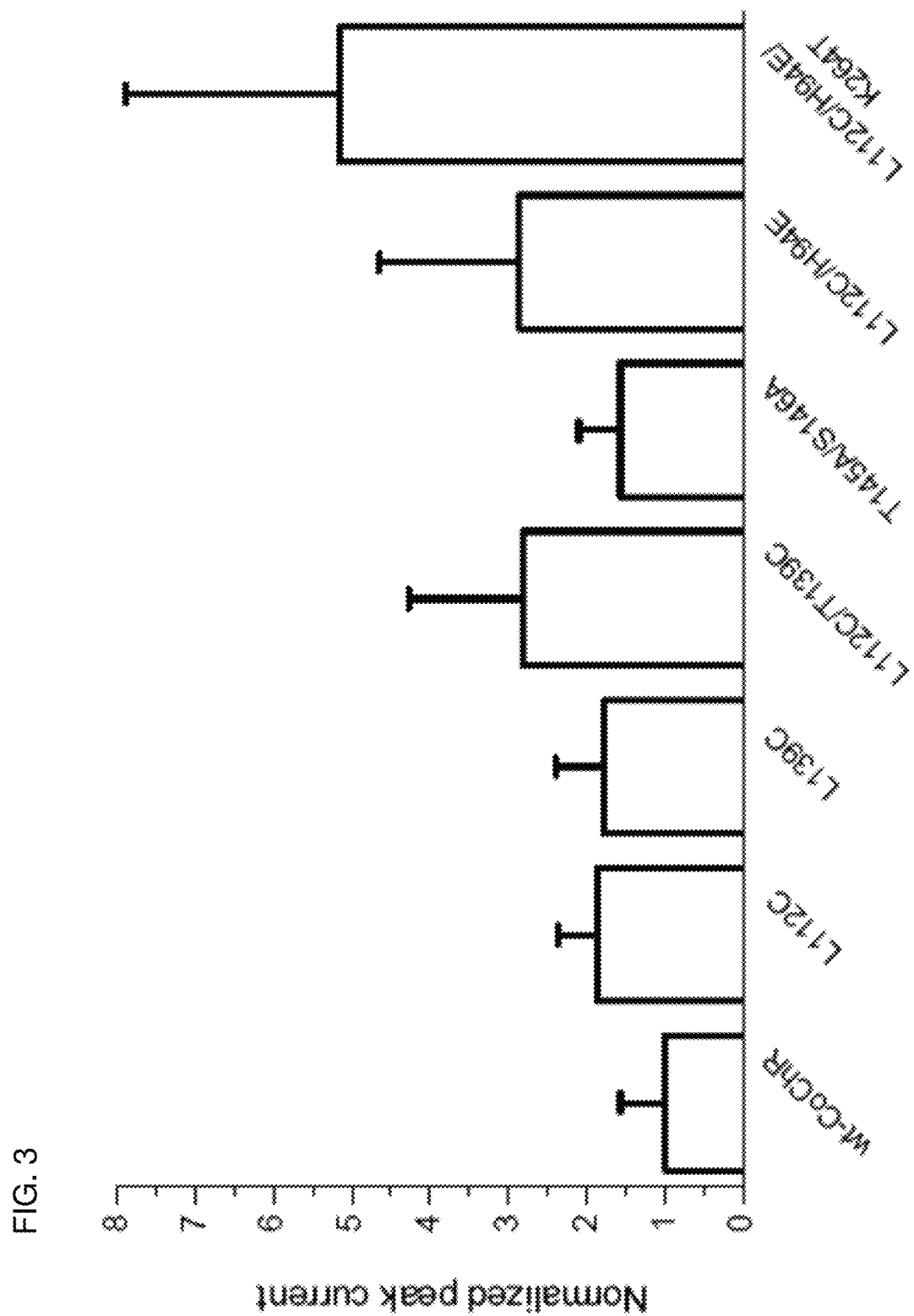
FIG. 3: Comparison of current amplitudes for wt-CoChR and its more light-sensitive mutants, CoChR-L112C (SEQ ID NO: 3), CoChR-T139C (SEQ ID NO: 5), CoChR-L112C/T139C (SEQ ID NO: 8), CoChR-T145A/S146A (SEQ ID NO: 6), CoChR-L112C/H94E (SEQ ID NO: 9), and CoChR-L112C/H94E/K264T (SEQ ID NO: 10), in HEK cell recordings. The currents were evoked by light at 480 nm with ND=2.5 ($4.8 \times 10^{15}$ photons/cm$^2$s) and normalized to that of wt-CoChR. Data are shown as the mean±SD.
Figure 4:
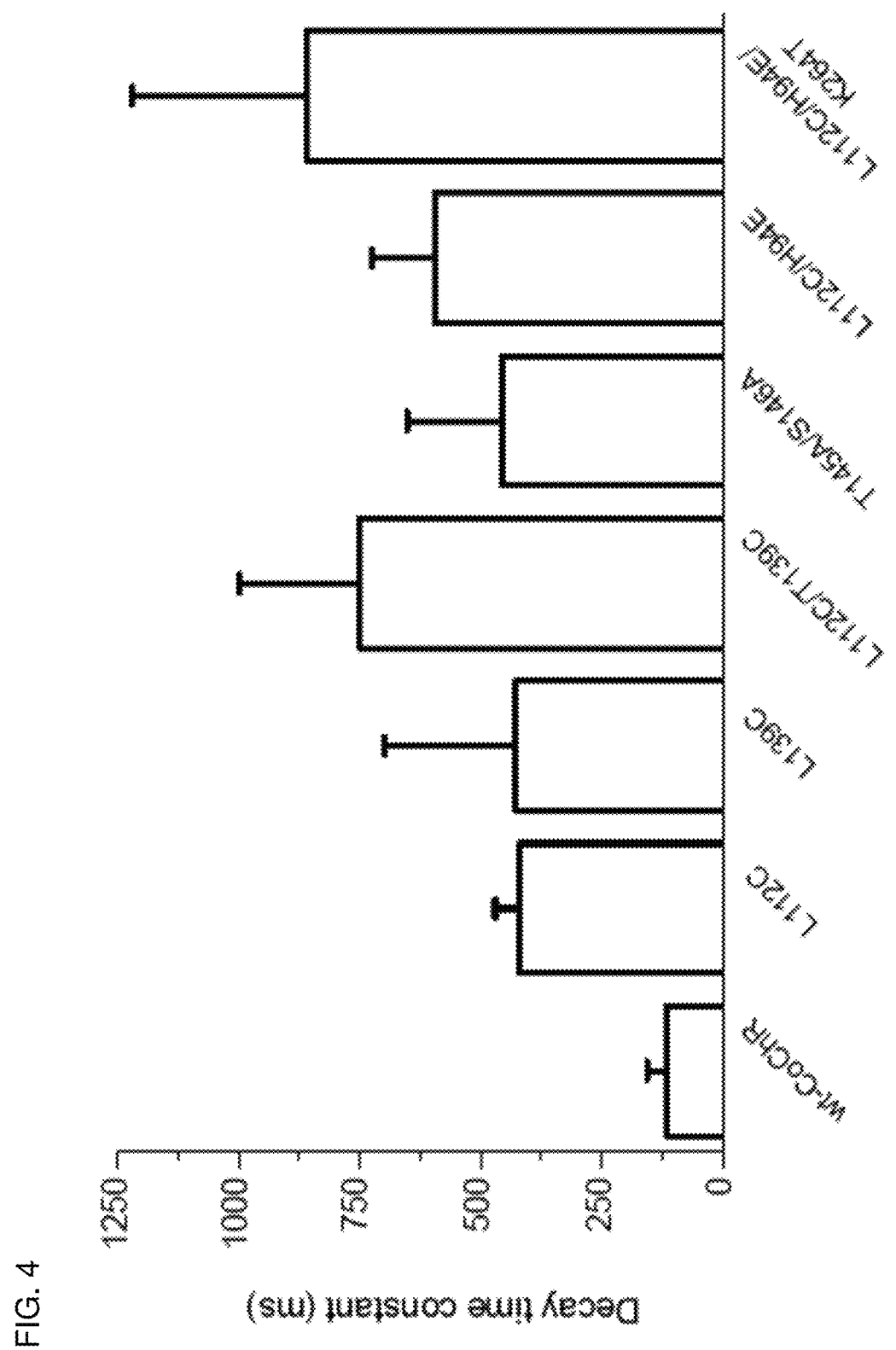
FIG. 4: Comparison of decay time constants (off rate) for wt-CoChR and its more light-sensitive mutants, CoChR-L112C, CoChR-T139C, CoChR-L112C/T139C, CoChR-T145A/S146A, CoChR-L112C/H94E, and CoChR-L112C/H94E/K264T, in HEK cell recordings. The currents were evoked by a 10 ms light pulse at ND=0 ($1.2 \times 10^{18}$ photons/cm$^2$s). Data are shown as the mean±SD.
Figure 5:
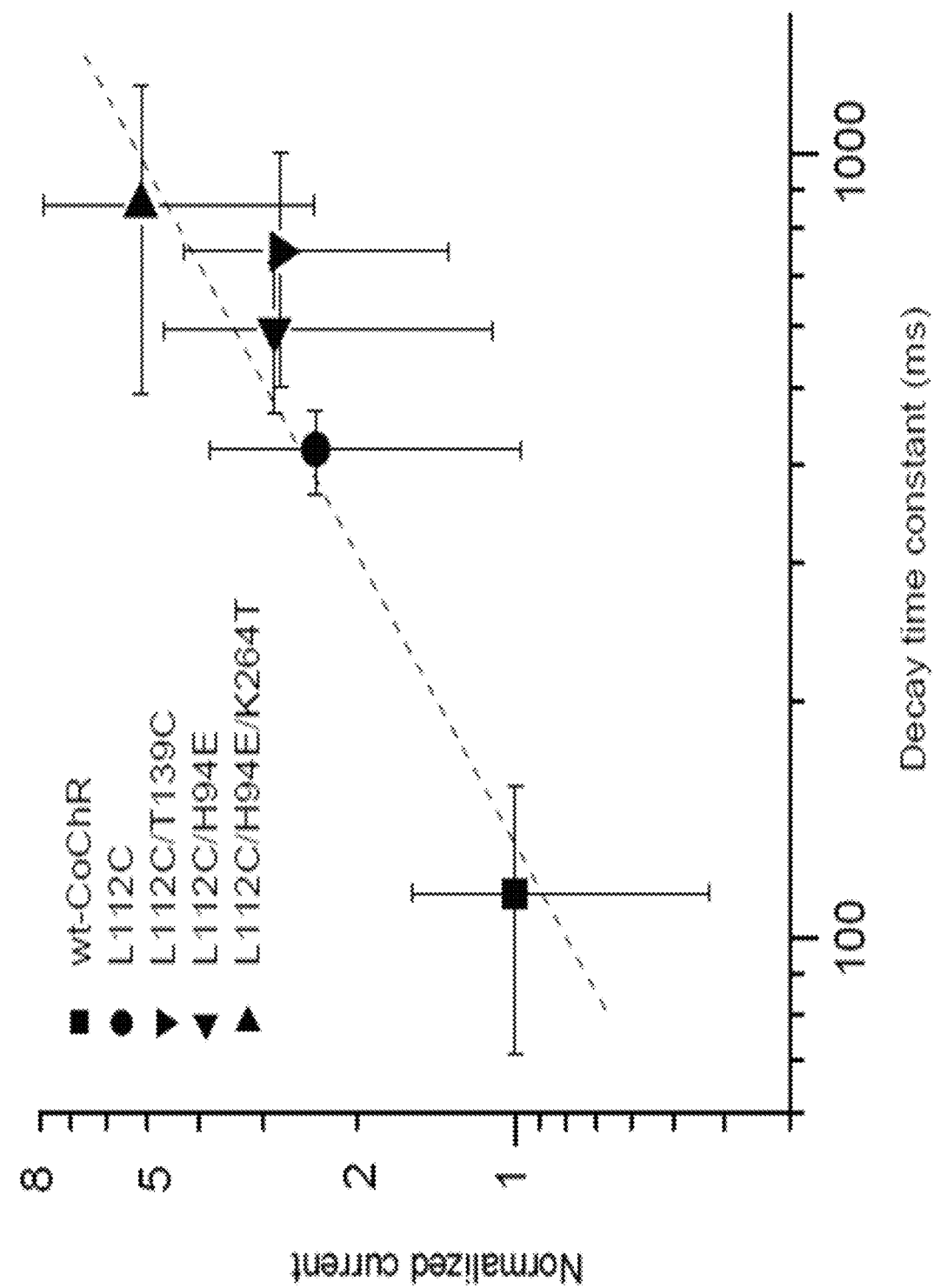
FIG. 5: The relationships of the light evoked current amplitude and decay time constant (or off rate) for wt-CoChR and its more light-sensitive mutants, CoChR-L112C, CoChR-L112C/T139C, CoChR-L112C/H94E, and CoChR-L112C/H94E/K264T, in HEK cell recordings.

The present invention is based, in part, on the unexpected discovery that mutations in a channelopsin variant from the green algae, Chloromonas oogama, CoChop, result in increased light sensitivity. The CoChop mutant amino acid and nucleic acid sequences according to the invention are referred to herein in as mCoChop. Wild-type CoChop is described for example WO2015/161308, the contents of which are incorporated by reference in its entirety. The mCoChop amino acid and nucleic acid sequences according to the invention are useful in any application in which a light activated ion channel is required.

In particular embodiments, the present invention features composition and methods for the treatment of retinal degenerative diseases, such as retinitis pigmentosa or age related macular degeneration. Additionally, other diseases and disorders that are the direct result of retinal degenerative diseases are also treated by the method of the invention. For example, advanced retinitis pigmentosa and other retinal degenerative condition results in macular degeneration.

The channelopsin variant, CoChop was first identified via de novo sequencing 127 algal transcriptomes. CoChop was identified by synthesizing and screening for photocurrents in HEK293 cells. (See, WO2015/161308, and Klapoetke et al. Nature Methods vol. 11, No. 3 2014, the contents of each are incorporated by reference in their entireties.)

As referred to herein, "CoChop" refers to the gene that encodes a channelopsin which then forms a channelrhodopsin (CoChR) once bound to retinal. Gene constructs of the present invention refer primarily to CoChop (i.e., without the retinal), and all CoChop mutants (mCoChop) disclosed herein form functional channelrhodopsins (ChR). The methods disclosed herein may include delivering, mCoChop to cells with or without exogenous retinal. It is understood that upon expression of mCoChop in cells (i.e., retinal neurons), endogenously available retinal binds to the mCoChop proteins of the present invention to form functional light-gated channels. As such, Chop proteins, as referred to herein, can also be synonymous with ChR.

The following sequences provide non-limiting examples of wild type CoChop mutant CoChop proteins, and polynucleotides encoding said WT and mutant Chop proteins of the invention, and forming WT and mutant ChRs of the invention.

```
Wild-type CoChR nucleic acid sequence
                                                    (SEQ ID NO: 1)
ATGCTGGGAAACGGCAGCGCCATTGTGCCTATCGACCAGTGCTTTTGCCTGGCTTGGACCGACAGCC

TGGGAAGCGATACAGAGCAGCTGGTGGCCAACATCCTCCAGTGGTTCGCCTTCGGCTTCAGCATCCT

GATCCTGATGTTCTACGCCTACCAGACTTGGAGAGCCACTTGCGGTTGGGAGGAGGTCTACGTCTGT
```

```
-continued
TGCGTCGAGCTGACCAAGGTCATCATCGAGTTCTTCCACGAGTTCGACGACCCCAGCATGCTGTACC

TGGCTAACGGACACCGAGTCCAGTGGCTGAGATACGCAGAGTGGCTGCTGACTTGTCCCGTCATCCT

GATCCACCTGAGCAACCTGACAGGCCTGAAGGACGACTACAGCAAGCGGACCATGAGGCTGCTGGTG

TCAGACGTGGGAACCATCGTGTGGGGAGCTACAAGCGCCATGAGCACAGGCTACGTCAAGGTCATCT

TCTTCGTGCTGGGTTGCATCTACGGCGCCAACACCTTCTTCCACGCCGCCAAGGTGTATATCGAGAG

CTACCACGTGGTGCCAAAGGGCAGACCTAGAACCGTCGTGCGGATCATGGCTTGGCTGTTCTTCCTG

TCTTGGGGCATGTTCCCCGTGCTGTTCGTCGTGGGACCAGAAGGATTCGACGCCATCAGCGTGTACG

GCTCTACCATTGGCCACACCATCATCGACCTCATGAGCAAGAATTGTTGGGGCCTGCTGGGACACTA

TCTGAGAGTGCTGATCCACCAGCACATCATCATCTACGGCGACATCCGCAAGAAGACCAAGATCAAC

GTGGCCGGCGAGGAGATGGAAGTGGAGACCATGGTGGACCAGGAGGACGAGGAGACAGTG

Wild-type CoChR amino acid sequence
                                               (SEQ ID NO: 2)
MLGNGSAIVPIDQCFCLAWTDSLGSDTEQLVANILQWFAFGFSILILMFYAYQTWRATCGWEEVYVC

CVELTKVIIEFFHEFDDPSMLYLANGHRVQWLRYAEWLLTCPVILIHLSNLTGLKDDYSKRTMRLLV

SDVGTIVWGATSAMSTGYVKVIFFVLGCIYGANTFFHAAKVYIESYHVVPKGRPRTVVRIMAWLFFL

SWGMFPVLFVVGPEGFDAISVYGSTIGHTIIDLMSKNCWGLLGHYLRVLIHQHIIIYGDIRKKTKIN

VAGEEMEVETMVDQEDEETV

Mutant CoChR amino acid sequence L112C
                                               (SEQ ID NO: 3)
MLGNGSAIVPIDQCFCLAWTDSLGSDTEQLVANILQWFAFGFSILILMFYAYQTWRATCGWEEVYVC

CVELTKVIIEFFHEFDDPSMLYLANGHRVQWLRYAEWLLTCPVICIHLSNLTGLKDDYSKRTMRLLV

SDVGTIVWGATSAMSTGYVKVIFFVLGCIYGANTFFHAAKVYIESYHVVPKGRPRTVVRIMAWLFFL

SWGMFPVLFVVGPEGFDAISVYGSTIGHTIIDLMSKNCWGLLGHYLRVLIHQHIIIYGDIRKKTKIN

VAGEEMEVETMVDQEDEETV

Mutant CoChR amino acid sequence C68S/V69I
                                               (SEQ ID NO: 4)
MLGNGSAIVPIDQCFCLAWTDSLGSDTEQLVANILQWFAFGFSILILMFYAYQTWRATCGWEEVYVC

SIELTKVIIEFFHEFDDPSMLYLANGHRVQWLRYAEWLLTCPVILIHLSNLTGLKDDYSKRTMRLLV

SDVGTIVWGATSAMSTGYVKVIFFVLGCIYGANTFFHAAKVYIESYHVVPKGRPRTVVRIMAWLFFL

SWGMFPVLFVVGPEGFDAISVYGSTIGHTIIDLMSKNCWGLLGHYLRVLIHQHIIIYGDIRKKTKIN

VAGEEMEVETMVDQEDEETV

Mutant CoChR amino acid sequence T139C
                                               (SEQ ID NO: 5)
MLGNGSAIVPIDQCFCLAWTDSLGSDTEQLVANILQWFAFGFSILILMFYAYQTWRATCGWEEVYVC

CVELTKVIIEFFHEFDDPSMLYLANGHRVQWLRYAEWLLTCPVILIHLSNLTGLKDDYSKRTMRLLV

SDVGCIVWGATSAMSTGYVKVIFFVLGCIYGANTFFHAAKVYIESYHVVPKGRPRTVVRIMAWLFFL

SWGMFPVLFVVGPEGFDAISVYGSTIGHTIIDLMSKNCWGLLGHYLRVLIHQHIIIYGDIRKKTKIN

VAGEEMEVETMVDQEDEETV

Mutant CoChR amino acid sequence T145A/S146A
                                               (SEQ ID NO: 6)
MLGNGSAIVPIDQCFCLAWTDSLGSDTEQLVANILQWFAFGFSILILMFYAYQTWRATCGWEEVYVC

CVELTKVIIEFFHEFDDPSMLYLANGHRVQWLRYAEWLLTCPVILIHLSNLTGLKDDYSKRTMRLLV

SDVGTIVWGAAAMSTGYVKVIFFVLGCIYGANTFFHAAKVYIESYHVVPKGRPRTVVRIMAWLFFL

SWGMFPVLFVVGPEGFDAISVYGSTIGHTIIDLMSKNCWGLLGHYLRVLIHQHIIIYGDIRKKTKIN

VAGEEMEVETMVDQEDEETV
```

```
Mutant CoChR amino acid sequence C68T/V69L
                                                           (SEQ ID NO: 7)
MLGNGSAIVPIDQCFCLAWTDSLGSDTEQLVANILQWFAFGFSILILMFYAYQTWRATCGWEEVYVC

TLELTKVIIEFFHEFDDPSMLYLANGHRVQWLRYAEWLLTCPVILIHLSNLTGLKDDYSKRTMRLLV

SDVGTIVWGATSAMSTGYVKVIFFVLGCIYGANTFFHAAKVYIESYHVVPKGRPRTVVRIMAWLFFL

SWGMFPVLFVVGPEGFDAISVYGSTIGHTIIDLMSKNCWGLLGHYLRVLIHQHIIIYGDIRKKTKIN

VAGEEMEVETMVDQEDEETV

Mutant CoChR amino acid sequence L112C/T139C
                                                           (SEQ ID NO: 8)
MLGNGSAIVPIDQCFCLAWTDSLGSDTEQLVANILQWFAFGFSILILMFYAYQTWRATCGW

LEVYVCCVELTKVIIEFFHEFDDPSMLYLANGHRVQWLRYAEWLLTCPVICIHLSNLTGLKD

DYSKRTMRLLVSDVGCIVWGATSAMSTGYVKVIFFVLGCIYGANTFFHAAKVYIESYHVVP

KGRPRTVVRIMAWLFFLSWGMFPVLFVVGPEGFDAISVYGSTIGHTIIDLMSKNCWGLLGH

YLRVLIHQHIIIYGDIRKKTKINVAGEEMEVETMVDQEDEETV

Mutant CoChR amino acid sequence L112C/H94E
                                                           (SEQ ID NO: 9)
MLGNGSAIVPIDQCFCLAWTDSLGSDTEQLVANILQWFAFGFSILILMFYAYQTWRATCGW

LEVYVCCVELTKVIIEFFHEFDDPSMLYLANGERVQWLRYAEWLLTCPVICIHLSNLTGLKD

DYSKRTMRLLVSDVGTIVWGATSAMSTGYVKVIFFVLGCIYGANTFFHAAKVYIESYHVVP

KGRPRTVVRIMAWLFFLSWGMFPVLFVVGPEGFDAISVYGSTIGHTIIDLMSKNCWGLLGH

YLRVLIHQHIIIYGDIRKKTKINVAGEEMEVETMVDQEDEETV

Mutant CoChR amino acid sequence L112C/H94E/K264T
                                                           (SEQ ID NO: 10)
MLGNGSAIVPIDQCFCLAWTDSLGSDTEQLVANILQWFAFGFSILILMFYAYQTWRATCGW

LEVYVCCVELTKVIIEFFHEFDDPSMLYLANGERVQWLRYAEWLLTCPVICIHLSNLTGLKD

DYSKRTMRLLVSDVGTIVWGATSAMSTGYVKVIFFVLGCIYGANTFFHAAKVYIESYHVVP

KGRPRTVVRIMAWLFFLSWGMFPVLFVVGPEGFDAISVYGSTIGHTIIDLMSKNCWGLLGH

YLRVLIHQHIIIYGDIRKTTKINVAGEEMEVETMVDQEDEETV
```

The present invention also encompasses CoChop proteins and nucleic acids that encode a biologically active fragment or a conservative amino acid substitution or other mutation variant of CoChop. Smaller fragments of wild-type CoChop, wherein at least one amino acid is mutated or conservatively substituted may also be useful in the present invention. In other embodiments, the CoChop polypeptides and nucleic acids of the present invention can be up to, or about, 275 amino acids long, 250 amino acids long, 225 amino acids long, 200 amino acids long, 175 amino acids long, or 160 amino acids long.

In some embodiments, the disclosure provides derivatives, variants, or mutants of one or more CoChop polypeptides disclosed herein. In some embodiments, the derivative, variant, or mutant contains one or more amino acid substitutions compared to the amino acid sequence of the native polypeptide (e.g. SEQ ID NO: 2). In some embodiments, one to 20 amino acids are substituted. In some embodiments, the derivative, variant, or mutant contains about 1, about 2, about 3, about 4, about 5, about 6, about 7, about 8, about 9, or about 10 amino acid substitutions compared to the amino acid sequence of the native therapeutic peptide agent. In some embodiments, the derivative, variant, or mutant contains one or more amino acid deletions compared to the amino acid sequence of the native polypeptide (e.g. SEQ ID NO: 2). In some embodiments, one to 20 amino acids are deleted compared to the amino acid sequence of the native polypeptide (e.g. SEQ ID NO: 2). In some embodiments, the derivative, variant, or mutant has about 1, about 2, about 3, about 4, about 5, about 6, about 7, about 8, about 9, or about 10 amino acid deletions compared to the amino acid sequence of the native polypeptide (e.g. SEQ ID NO: 2). In some embodiments, one to ten amino acids are deleted at either terminus compared to the amino acid sequence of the native polypeptide (e.g. SEQ ID NO: 2). In some embodiments, one to ten amino acids are deleted from both termini compared to the amino acid sequence of the native polypeptide (e.g. SEQ ID NO: 2). In some embodiments, the amino acid sequence of the derivative, variant, or mutant is at least about 70% identical to the amino acid sequence of the native polypeptide (e.g. SEQ ID NO: 2). In some embodiments, the amino acid sequence of the derivative, variant, or mutant is about 70%, about 80%, about 85%, about 90%, about 95%, about 96%, about 97%, about 98%, or about 99% identical to the amino acid sequence of the native polypeptide (e.g. SEQ ID NO: 2).

Mutant CoChop proteins of the invention also demonstrate slower channel kinetics. Higher light sensitivity was found to correlate with slower channel kinetics, indicating a trade-off between light sensitivity and channel kinetics. mCoChop proteins that form the ChR proteins of the present invention may also comprise additional mutations or modifications that may improve channel kinetics, or increase the deactivation rate. Particularly preferred CoChop mutants balance the threshold of light sensitivity with channel kinetics.

For example, mutant ChR proteins of the invention achieve greater light sensitivity through the prolongation of the channel open state. Consequently, each mutant ChR channel conducts a greater photocurrent than a wild type ChR channel when activated by the same light intensities. Therefore, the mutant channels are activated by light intensities that are lower than those required for activation of the wild type ChR channels. Quantitatively, detectable spiking activity of retinal ganglion cells expressing mutant ChR proteins can be elicited by a light intensity that is 1.5-2 log units lower than the light intensity required to elicit spiking activity from retinal ganglion cells expressing wild type ChR. Thus, the light intensities required to activate the mutant ChR proteins are close to or fall within the range of normal outdoor lighting conditions.

Nucleic Acids, Vectors and Recombinant Viruses

In some aspect of the invention, the compositions and methods of the disclosure provide for the delivery of a nucleic acid encoding mCoChop (mutant CoChop) to cells in a subject or patient in need thereof. In some cases, delivery of the nucleic acid may be referred to as gene therapy.

The composition and methods of the disclosure provide for any suitable method for delivery of the mCoChop nucleic acid. In some cases, delivery of the nucleic acid may be performed using any suitable "vector" (sometimes also referred to as "gene delivery" or "gene transfer" vehicle). Vector, delivery vehicle, gene delivery vehicle or gene transfer vehicle, may refer to any suitable macromolecule or complex of molecules comprising a polynucleotide to be delivered to a target cell. In some cases, a target cell may be any cell to which the nucleic acid or gene is delivered. The polynucleotide to be delivered may comprise a coding sequence of interest in gene therapy, such as the mCoChop gene.

For example, suitable vectors may include but are not limited to, viral vectors such as adenoviruses, adeno-associated viruses (AAV), and retroviruses, liposomes, other lipid-containing complexes, and other macromolecular complexes capable of mediating delivery of a polynucleotide to a target cell.

In some cases, a vector may be an organic or inorganic molecule. In some cases, a vector may be small molecule (i.e. <5 kD), or a macromolecule (i.e. >5 kD). For example a vector may include but is not limited to inert, non-biologically active molecules such as metal particles. In some cases, a vector may be gold particles.

In some aspects, a vector may comprise a recombinant viral vector that incorporates one or more nucleic acids. As described herein, nucleic acids may refer to polynucleotides. Nucleic acid and polynucleotide may be used interchangeably. In some cases nucleic acids may comprise DNA or RNA. In some aspects, nucleic acids may include DNA or RNA for the expression of mCoChop. In some aspects RNA nucleic acids may include but are not limited to a transcript of a gene of interest (e.g. mCoChop), introns, untranslated regions, termination sequences and the like. In other cases, DNA nucleic acids may include but are not limited to sequences such as hybrid promoter gene sequences, strong constitutive promoter sequences, the gene of interest (e.g. mCoChop), untranslated regions, termination sequences and the like. In some cases, a combination of DNA and RNA may be used.

As described in the disclosure herein, the term "expression construct" is meant to include any type of genetic construct containing a nucleic acid or polynucleotide coding for gene products in which part or all of the nucleic acid encoding sequence is capable of being transcribed. The transcript may be translated into a protein. In some aspects it may be partially translated or not translated. In certain aspects, expression includes both transcription of a gene and translation of mRNA into a gene product. In other aspects, expression only includes transcription of the nucleic acid encoding genes of interest.

In one aspect, the present disclosure provides a recombinant virus, such as adeno-associated virus (rAAV) as a vector to mediate the expression of mCoChop.

In some cases, the viral vector of the disclosure may be measured as pfu (plaque forming units). In some cases, the pfu of recombinant virus, or viral vector of the compositions and methods of the disclosure may be about $10^8$ to about $5 \times 10^{10}$ pfu. In some cases, recombinant viruses of this disclosure are at least about $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, and $5 \times 10^{10}$ pfu. In some cases, recombinant viruses of this disclosure are at most about $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, and $5 \times 10^{10}$ pfu.

In some cases, the viral vector of the disclosure may be measured as vector genomes. In some cases, recombinant viruses of this disclosure are $1 \times 10^{10}$ to $3 \times 10^{12}$ vector genomes. In some cases, recombinant viruses of this disclosure are $1 \times 10^9$ to $3 \times 10^{13}$ vector genomes. In some cases, recombinant viruses of this disclosure are $1 \times 10^8$ to $3 \times 10^{14}$ vector genomes. In some cases, recombinant viruses of the disclosure are at least about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ vector genomes.

In some cases, the viral vector of the disclosure may be measured using multiplicity of infection (MOI). In some cases, MOI may refer to the ratio, or multiple of vector or viral genomes to the cells to which the nucleic may be delivered. In some cases, the MOI may be $1 \times 10^6$. In some cases, the MOI may be $1 \times 10^5$-$1 \times 10^7$. In some cases, the MOI may be $1 \times 10^4$-$1 \times 10^8$. In some cases, recombinant viruses of the disclosure are at least about $1 \times 10^1$, $1 \times 10^2$, $1 \times 10^3$, $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, and $1 \times 10^{18}$ MOI. In some cases, recombinant viruses of this disclosure are $1 \times 10^8$ to $3 \times 10^{14}$ MOI.

In some aspects the nucleic acid may be delivered without the use of a virus (i.e. with a non-viral vector), and may be measured as the quantity of nucleic acid. Generally, any suitable amount of nucleic acid may be used with the compositions and methods of this disclosure. In some cases, nucleic acid may be at least about 1 pg, 10 pg, 100 pg, 1 pg, 10 pg, 100 pg, 200 pg, 300 pg, 400 pg, 500 pg, 600 pg, 700 pg, 800 pg, 900 pg, 1 µg, 10 µg, 100 µg, 200 µg, 300 µg, 400 µg, 500 µg, 600 µg, 700 µg, 800 µg, 900 µg, 1 ng, 10 ng, 100 ng, 200 ng, 300 ng, 400 ng, 500 ng, 600 ng, 700 ng, 800 ng, 900 ng, 1 mg, 10 mg, 100 mg, 200 mg, 300 mg, 400 mg, 500 mg, 600 mg, 700 mg, 800 mg, 900 mg 1 g, 2 g, 3 g, 4 g, or 5 g. In some cases, nucleic acid may be at most about 1 pg, 10 pg, 100 pg, 1 pg, 10 pg, 100 pg, 200 pg, 300 pg, 400 pg, 500 pg, 600 pg, 700 pg, 800 pg, 900 pg, 1 µg, 10 µg, 100 µg, 200 µg, 300 µg, 400 µg, 500 µg, 600 µg, 700 µg, 800 µg, 900 µg, 1 ng, 10 ng, 100 ng, 200 ng, 300 ng, 400 ng, 500 ng, 600 ng, 700 ng, 800 ng, 900 ng, 1 mg, 10 mg, 100 mg, 200 mg, 300 mg, 400 mg, 500 mg, 600 mg, 700 mg, 800 mg, 900 mg, 1 g, 2 g, 3 g, 4 g, or 5 g. In some aspects, a self-complementary vector (sc) may be used. The use of self-complementary AAV vectors may bypass the requirement for viral second-strand DNA synthesis and may lead to greater rate of expression of the transgene protein, as provided by Wu, Hum Gene Ther. 2007, 18(2):171-82, incorporated by reference herein.

The compositions and methods of the disclosure provide for any suitable viral nucleic acid delivery systems including but not limited to use of at least one of an adeno-associated virus (AAV), adenovirus, helper-dependent adenovirus, retrovirus, herpes simplex virus, lentivirus, poxvirus, hemagglutination virus of Japan-liposome (HVJ) complex, Moloney murine leukemia virus, and HIV-based virus. Preferably, the viral vector comprises a strong eukaryotic promoter operably linked to the polynucleotide.

Generally, any suitable viral vectors may be engineered to be optimized for use with the compositions and methods of the disclosure. For example, viral vectors derived from adenovirus (Ad) or adeno-associated virus (AAV) may be used. Both human and non-human viral vectors can be used and the recombinant viral vector can be altered such that it may be replication-defective in humans. Where the vector is an adenovirus, the vector can comprise a polynucleotide having a promoter operably linked to a gene encoding the mCoChop protein and is replication-defective in humans.

To combine advantageous properties of two viral vector systems, hybrid viral vectors may be used to deliver a nucleic acid encoding a mCoChop protein to a target cell or tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000.

Retroviral genomes contained within an adenovirus may integrate within the target cell genome and effect stable gene expression.

Replication-defective recombinant adenoviral vectors can be produced in accordance with known techniques. See, Quantin, et al., Proc. Natl. Acad. Sci. USA, 89:2581-2584 (1992); Stratford-Perricadet, et al., J. Clin. Invest., 90:626-630 (1992); and Rosenfeld, et al., Cell, 68:143-155 (1992).

Additionally preferred vectors may include but are not limited to viral vectors, fusion proteins and chemical conjugates. Retroviral vectors include Moloney murine leukemia viruses and HIV-based viruses. In some cases a HIV-based viral vector may be used, wherein the HIV-based viral vector comprises at least two vectors wherein the gag and pol genes are from an HIV genome and the env gene is from another virus. DNA viral vectors may be used. These vectors include pox vectors such as orthopox or avipox vectors, herpesvirus vectors such as a herpes simplex I virus (HSV) vector [Geller, A. I. et al., J. Neurochem, 64: 487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A.: 90 7603 (1993); Geller, A. I., et al., Proc Natl. Acad. Sci. USA: 87:1149 (1990)], Adenovirus Vectors [LeGal LaSalle et al., Science, 259:988 (1993); Davidson, et al., Nat. Genet. 3: 219 (1993); Yang, et al., J. Virol. 69: 2004 (1995)] and Adeno-associated Virus Vectors [Kaplitt, M. G., et al., Nat. Genet. 8:148 (1994)], incorporated by reference herein.

Other viral vectors that can be used in accordance with the present disclosure include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid.

Retroviruses, such as C-type retroviruses and lentiviruses, may also be used in the disclosure. For example, retroviral vectors may be based on murine leukemia virus (MLV)., as provided by Hu and Pathak, Pharmacol. Rev. 52:493511, 2000 and Fong et al., Crit. Rev. Ther. Drug Carrier Syst. 17:1-60, 2000, incorporated by reference herein. MLV-based vectors may contain up to 8 kb of heterologous (therapeutic) DNA in place of the viral genes. Additional retroviral vectors may be used including but not limited to replication-defective lentivirus-based vectors, including human immunodeficiency (HIV)-based vectors, as provided by Vigna and Naldini, J. Gene Med. 5:308-316, 2000 and Miyoshi et al., J. Virol. 72:8150-8157, 1998, incorporated by reference herein. Lentiviral vectors may be advantageous in that they are capable of infecting both actively dividing and non-dividing cells. They may also be highly efficient at transducing human epithelial cells.

Lentiviral vectors for use in the disclosure may be derived from human and non-human (including SIV) lentiviruses. Examples of lentiviral vectors include nucleic acid sequences required for vector propagation as well as a tissue-specific promoter operably linked to a mCoChop gene. Nucleic acid sequences may include the viral LTRs, a primer binding site, a polypurine tract, att sites, and an encapsidation site.

A lentiviral vector may be packaged into any suitable lentiviral capsid. The substitution of one particle protein with another from a different virus is referred to as "pseudo-typing". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN), may also be used in the disclosure. Use of alphaviruses is described in Lundstrom, K., Intervirology 43:247-257, 2000 and Perri et al., Journal of Virology 74:9802-9807, 2000, incorporated by reference herein.

Recombinant, replication-defective alphavirus vectors may be advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

Pox viral vectors may introduce a gene into the cell's cytoplasm. Avipox virus vectors may result in only a short-term expression of the gene or nucleic acid. Adenovirus vectors, adeno-associated virus vectors and herpes simplex virus (HSV) vectors may be used with the compositions and methods of the disclosure. The adenovirus vector may result in a shorter-term expression (e.g., less than about a month) than adeno-associated virus, in some aspects, and may exhibit much longer expression. The particular vector chosen may depend upon the target cell and the condition being treated.

Adeno-associated viruses (AAV) are small non-enveloped single-stranded DNA viruses. They are non-pathogenic human parvoviruses and may be dependent on helper viruses, including adenovirus, herpes simplex virus, vaccinia virus and CMV, for replication. Exposure to wild-type (wt) AAV is not associated or known to cause any human pathologies and is common in the general population, usually occurring in the first decade of life in association with an adenoviral infection.

As described herein, "AAV" refers to Adeno-associated virus "rAAV" refers to a recombinant adeno-associated virus.

In some cases, the wild-type AAV encodes rep and cap genes. The rep gene is required for viral replication and the cap gene is required for synthesis of capsid proteins. Through a combination of alternative translation start and splicing sites, the small genome may be able to express four rep and three cap gene products. The rep gene products and sequences in the inverted terminal repeats (145 bp ITRs, which flank the genome) may be critical in this process. To date, 11 serotypes of AAV have been isolated. The compositions and methods of the disclosure provide for use of any suitable AAV serotype. In some aspects, the AAV is selected from the group consisting of: AAV1, AAV2, AAV2.5, AAV3, AAV4, AAV5, AAV6, AAV7, AAV8, AAV9, AAV10, AAV11, AAV12, rh10, and hybrids thereof. AAV2 may be used with composition and methods of the disclosure.

AAV2 is the most characterized. rAAV2 has been shown to be able to mediate long-term transgene expression in the eyes of many species of animals. In rats, rAAV mediated reporter gene (green fluorescent protein) was still present at 18 months post injection. In monkeys, the same reporter gene was present at 17 months post injection.

Vectors can comprise components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., Lupton, S., WO 92/08796, published May 29, 1992; and Lupton, S., WO 94/28143, published Dec. 8, 1994). Examples of negative selectable markers may include the inclusion of resistance genes to antibiotics, such as ampicillin or kanamycin. Such marker genes can provide an added measure of control that can be advantageous in gene therapy contexts. A large variety of such vectors are known in the art and are generally available.

In many of the viral vectors compatible with methods of the disclosure, one or more promoters can be included in the vector to allow more than one heterologous gene to be expressed by the vector. Further, the vector can comprise a sequence which encodes a signal peptide or other moiety which facilitates expression of the mCoChop protein from the target cell.

The nucleic acid encoding a gene product may be under transcriptional control by a promoter. A "promoter", as provided herein, refers to a suitable DNA sequence required to initiate transcription of a gene. The phrase "under transcriptional control" means that the promoter is in the correct location and orientation in relation to the nucleic acid to control RNA polymerase initiation and expression of the gene. In some cases, promoter may include a "strong" or constitutively active promoter. For example, the CMV promoter may be used as known in the art a constitutively active promoter. In some cases, the CMV promoter may comprise additional regulatory elements for promoting expression.

In some cases a promoter may refer to a "weak" promoter, or sequence that yields lower levels of mCoChop protein than a strong promoter. In some cases a promoter may be used such that the promoter drives selective expression of mCoChop. In some cases a promoter or other regulatory elements used in combination with other sequences as described herein may be used to drive selective expression of mCoChop in an eye cell, or eye tissue.

Additionally, "promoter", may also be used herein interchangeably to refer to any additional suitable transcriptional control modules that may be present around the initiation site for RNA polymerases. The compositions and methods of this disclosure may use any suitable promoters and transcriptional control modules for expression of a transgene. Additional transcriptional control modules may include but are not limited to elements such as HSV thymidine kinase (tk) and SV40 early transcription units. Generally, promoters may be composed of discrete functional modules, each consisting of approximately 7-20 bp of DNA, or 20-5000 bp of DNA, and contain one or more recognition sites for transcriptional activator or repressor proteins. The composition and methods of the disclosure provide for any suitable regulatory sequences or combination thereof. In some cases, these transcriptional control module sequences may be referred to or identified as enhancer or repressor sequences.

At least one module in each promoter functions to position the start site for RNA synthesis. One example is the TATA box. Other examples may include some promoters that lack a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Generally, these are located in a region 30-110 bp upstream of the start site, although a number of promoters may contain functional elements downstream of the start site as well. The spacing between promoter elements frequently may be flexible, so that promoter function is preserved when elements are inverted or moved relative to one another. In the tk promoter for example, the spacing between promoter elements can be increased to 50 bp apart before activity begins to decline. Depending on the promoter, individual elements may position to function either co-operatively or independently to activate transcription.

The compositions and methods of the disclosure provide for any suitable sequences for the control of expression of a nucleic acid sequence of interest in the targeted cell. Thus, where a human cell is targeted, the nucleic acid coding region may be engineered to be adjacent to and under the control of a promoter that is capable of being expressed in a human cell. Generally, such a promoter might include either a human or viral promoter.

In various aspects of the disclosure, the human cytomegalovirus (CMV) immediate early (IE) enhancer, a chicken β-actin promoter, a chicken β-actin exon 1, a hybrid chicken β-actin and rabbit β-globin intron, a simian virus 40 polyadenylation signal can be used to obtain a high level of expression of the coding sequence of interest (e.g. mCo-Chop).

The use of other viral or mammalian cellular or bacterial phage promoters which are well-known in the art to achieve expression of a coding sequence of interest is contemplated as well, provided that the levels of expression are sufficient for a given purpose. In some aspects, prokaryotic regulatory sequences may be present in the vector, such as the T7 RNA polymerase promoter sequence. In other aspects, the vector is free from such regulatory sequences. By employing a promoter with known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it may be desirable to prohibit or reduce expression of one or more of the transgenes. Examples of transgenes that may be toxic to the producer cell line are pro-apoptotic and cytokine genes. Several inducible promoter systems are available for production of viral vectors where the transgene product may be toxic. The composition and methods of the disclosure provide for any suitable combination of promoter sequence, regulatory sequences and transgene. In some cases, a combination of sequences may result in no toxicity to the cell. In some cases, a combination of sequences may result in high toxicity to the cell. In some cases, a combination of sequences may result in moderate levels of toxicity in the cell.

In some circumstances, it may be desirable to regulate expression of a transgene in a gene therapy vector. For example, different viral promoters with varying strengths of activity may be utilized depending on the level of expression desired. In mammalian cells, the CMV immediate early promoter may be used to provide strong transcriptional activation. Modified versions of the CMV promoter that are less potent have also been used when reduced levels of expression of the transgene are desired. When expression of a transgene in hematopoietic cells is desired, retroviral promoters such as the LTRs (Long Terminal Repeat) from MLV or MMTV are often used. Other viral promoters that may be used depending on the desired effect include SV40, RSV LTR, HIV-1 and HIV-2 LTR, adenovirus promoters such as from the E1A, E2A, or MLP region, AAV LTR, cauliflower mosaic Virus, HSV-TK, and avian sarcoma virus.

In some cases, promoters or regulatory sequence elements may be used to direct selective expression in eye cells or eye tissue. For example, promoter, sequence elements or regulatory sequences found in specific eye cell types, such as retinal pigment epithelial cells, may be used in a suitable expression construct (e.g., the RPE65 or VMD2 promoter).

The selection of appropriate promoters can be readily accomplished. In some cases a high expression, or strong promoter may be used.

Other elements that can enhance expression can also be included such as an enhancer or a system that results in high levels of expression such as a tat gene and tar element. This cassette can then be inserted into a vector, e.g., a plasmid vector such as, pUC19, pUC118, pBR322, or other known plasmid vectors, that includes, for example, an E. coli origin of replication. See, Sambrook, et al., Molecular Cloning: A Laboratory Manual, Cold Spring Harbor Laboratory press, (1989). Promoters are discussed infra. The plasmid vector may also include a selectable marker such as the .beta.-lactamase gene for ampicillin resistance, provided that the marker polypeptide does not adversely affect the metabolism of the organism being treated. The cassette can also be bound to a nucleic acid binding moiety in a synthetic delivery system, such as the system disclosed in WO 95/22618, incorporated by reference herein. Generally promoter sequences and/or any associated regulatory sequences may comprise about at least 150 bp, 200 bp, 300 bp, 400 bp, 500 bp, 600 bp, 700 bp, 800 bp, 900 bp, 1000 bp, 2000 bp, 3000 bp, 4000 bp, 5000 bp or 10000 bp. Promoter sequences and any associated regulatory sequences, may comprise about at most 150 bp, 200 bp, 300 bp, 400 bp, 500 bp, 600 bp, 700 bp, 800 bp, 900 bp, 1000 bp, 2000 bp, 3000 bp, 4000 bp, 5000 bp or 10000 bp.

In some aspects, the recombinant virus or plasmid comprises a promoter selected from cytomegalovirus (CMV) promoter, Rous sarcoma virus (RSV) promoter, and MMT promoter, EF-1 alpha promoter, UB6 promoter, chicken beta-actin promoter, CAG promoter, RPE65 promoter and opsin promoter.

In some aspects, an antibiotic marker is used in the process for production of the recombinant virus. Antibiotic resistance markers may be used to identify positive transgenic cells in the generation of recombinant virus. For example markers conferring resistance may include but are not limited to kanamycin, gentamicin, ampicillin, chloramphenicol, tetracycline, doxycycline, or hygromycin. In some aspects, the antibiotic resistance gene is a non-beta-lactam antibiotic resistance gene such as kanamycin.

In some aspects, the recombinant virus and/or plasmid used to generate recombinant virus, comprise a sequence encoding a replication origin sequence, such as those provided herein. Origin of replication sequences, generally provide sequence useful for propagating a plasmid.

In some aspects, the recombinant virus and/or plasmid used to generate recombinant virus, comprise an enhancer, such as those provided herein. Preferably the enhancer is a CMV immediate early enhancer.

In some aspects, the recombinant virus and/or plasmid used to generate recombinant virus, comprise a poly A (polyadenylation) sequence, such as those provided herein (e.g. SV40 poly A sequence.). Generally, any suitable polyA sequence may be used for the desired expression of the transgene (i.e. mCoChop). For example, in some cases, the present disclosure provides for a sequence comprising SV40 polyA sequence, or portion of SV40 polyA sequence. In some cases, the present disclosure provides for polyA sequences comprising a combination of one or more polyA sequences or sequence elements. In some cases, no polyA sequence is used. In some cases one or more polyA sequences may be referred to as untranslated regions (UTRs), 3' UTRs, or termination sequences. Preferably, a SV40 polyA sequence is used.

A polyA sequence may comprise a length of 1-10 bp, 10-20 bp, 20-50 bp, 50-100 bp, 100-500 bp, 500 bp-1 Kb, 1 Kb-2 Kb, 2 Kb-3 Kb, 3 Kb-4 Kb, 4 Kb-5 Kb, 5 Kb-6 Kb, 6 Kb-7 Kb, 7 Kb-8 Kb, 8 Kb-9 Kb, and 9 Kb-10 Kb in length. A polyA sequence may comprise a length of at least 1 bp, 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 Kb, 2 Kb, 3 Kb, 4 Kb, 5 Kb, 6 Kb, 7 Kb, 8 Kb, 9 Kb, and 10 Kb in length. A polyA sequence may comprise a length of at most 1 bp, 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 Kb, 2 Kb, 3 Kb, 4 Kb, 5 Kb, 6 Kb, 7 Kb, 8 Kb, 9 Kb, and 10 Kb in length.

In some cases, polyA sequences may be optimized for various parameters affecting protein expression, including but not limited to mRNA half-life of the transgene in the cell, stability of the mRNA of the transgene or transcriptional regulation. For example, polyA sequences maybe altered to increase mRNA transcript of the transgene, which may result in increased protein expression. In some cases, the polyA sequences maybe altered to decrease the half-life of the mRNA transcript of the transgene, which may result in decreased protein expression.

In certain aspects of the disclosure, the use of internal ribosome entry site (IRES) or foot-mouth disease virus (FMDV) elements may be used to create multigene, or polycistronic, messages. IRES elements are able to bypass the ribosome scanning model of 5' methylated Cap dependent translation and begin translation at internal sites. IRES elements from two members of the picornavirus family (poliovirus and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame may be accessible to ribosomes for efficient translation. Multiple genes can be efficiently expressed using a single promoter/enhancer to transcribe a single message. An alternative system for co-expression of two proteins in gene therapy delivery vectors is the FMDV 2A system. The FMDV 2A system employs a retroviral plasmid vector in which two genes may be linked to a nucleotide sequence encoding the 2A sequence from the picornavirus foot-and-mouth disease virus. Transcription and translation gives rise to a bicistronic mRNA and two independent protein products.

Any heterologous open reading frame can be linked to IRES elements. This may include genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

In some aspects, the recombinant virus and/or plasmid used to generate recombinant virus, comprise a polynucleotide encoding a human mCoChop protein or a functional fragment thereof.

In some aspects, the recombinant virus and/or plasmid used to generate recombinant virus, comprise a regulatory nucleic acid fragment that is capable of directing selective expression of the mCoChop protein in an eye cell.

In some aspects, the recombinant virus and/or plasmid used to generate recombinant virus, may comprise one or more untranslated regions (UTR) or sequences. Generally, any suitable UTR sequence may be used for the desired optimal expression of the transgene (i.e. mCoChop). For example, in some cases, UTR regions or sequences may comprise native sequences. In some cases, UTR sequences may be sequences as found upstream (5' UTR) or downstream (3'UTR) of the human mCoChop gene as found in human genomic sequence or portions thereof. In other cases, UTR sequences may comprise non-native sequences, such as found upstream or downstream of genes other than mCoChop or comprise sequences further comprising a combination of one or more UTR sequence elements as further described herein. In some cases, only a 5' UTR sequence is used. In some cases, only a 3' UTR sequence is used. In some cases, no UTR sequences are used.

A UTR sequence may comprise a length of 1-10 bp, 10-20 bp, 20-50 bp, 50-100 bp, 100-500 bp, 500 bp-1 Kb, 1 Kb-2 Kb, 2 Kb-3 Kb, 3 Kb-4 Kb, 4 Kb-5 Kb, 5 Kb-6 Kb, 6 Kb-7 Kb, 7 Kb-8 Kb, 8 Kb-9 Kb, and 9 Kb-10 Kb in length. A UTR sequence may comprise a length of at least 1 bp, 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 Kb, 2 Kb, 3 Kb, 4 Kb, 5 Kb, 6 Kb, 7 Kb, 8 Kb, 9 Kb, and 10 Kb in length. A UTR sequence may comprise a length of at most 1 bp, 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 Kb, 2 Kb, 3 Kb, 4 Kb, 5 Kb, 6 Kb, 7 Kb, 8 Kb, 9 Kb, and 10 Kb in length.

In some cases, variations of either the 5'UTR and/or 3'UTR may be optimized for a desired level of protein expression. In some cases, 3'UTR sequences may be optimized for various parameters affecting protein expression, including but not limited to mRNA half-life of the transgene in the cell, stability or secondary structure of the mRNA of the transgene or conditional regulation (e.g. binding of various factors to modulate translation). For example, the 3'UTR sequence maybe altered to increase the half-life of the mRNA transcript of the transgene, which may result in increased protein expression. In some cases, the 3'UTR sequence maybe altered to decrease the half-life of the mRNA transcript of the transgene, which may result in decreased protein expression.

Generally, 3' UTRs sequences may comprise various sequence elements. The present disclosure provides for 3' UTR sequences that may include but are not limited to sequence elements such as one or more polyadenylation signals, linker sequences, spacer sequences, SECIS elements, AU-rich or ARE sequences or miRNA or RNAi binding sequences, transcription terminator sequences, 3' termination sequences or variants and/or combinations thereof.

In some cases, 5'UTR sequences may be optimized for various parameters affecting protein expression, including but not limited to mRNA half-life of the transgene in the cell, stability or secondary structure of the mRNA of the transgene or transcriptional regulation. For example, the 5'UTR sequences may be altered to increase translation efficiency of mRNA transcript of the transgene, which may result in increased protein expression. In some cases, the 5'UTR sequences maybe altered to decrease translation efficiency of mRNA transcript of the transgene, which may result in decreased protein expression.

Generally, 5' UTRs sequences may comprise various sequence elements. The present disclosure provides for 5' UTR sequences that may include but are not limited to sequence elements such as one or more ribosome binding sites (RBS), linker sequences, spacer sequences, regulatory sequences, regulatory response elements, riboswitches, sequences that promote or inhibit translation initiation, regulatory sequences for mRNA transport or variants and/or combinations thereof.

In some aspects, the recombinant virus and/or plasmid used to generate recombinant virus, may comprise one or more linker or spacer sequences. As described herein, linker sequence or spacer sequence may be used interchangeably. Generally, a linker sequence or spacer sequence may be any suitable sequence used to create a non-contiguous sequence between at least two sequence elements. Generally, any suitable linker or spacer sequence may be used to create non-contiguous sequences. For example, in some cases, linker sequences may be randomly generated sequence. In some cases, linker sequence may be non-specific sequence optimized to prevent formation of secondary structure or intramolecular interactions that may adversely affect protein expression. In some cases, linker sequences may comprise any additional functional sequence elements, including but not limited to introns, regulatory sequences, enhancers or the like. Functional elements in linker sequences may be used for the desired optimal production of virus and/or expression of transgene expression. In some cases, linker sequences are cloning sites, remnants of prior cloning sites or other non-significant sequences and the insertion of such linkers between any two sequence elements is optional.

A linker sequence may comprise a length of 1-10 bp, 10-20 bp, 20-50 bp, 50-100 bp, 100-500 bp, 500 bp-1 Kb, 1 Kb-2 Kb, 2 Kb-3 Kb, 3 Kb-4 Kb, 4 Kb-5 Kb, 5 Kb-6 Kb, 6 Kb-7 Kb, 7 Kb-8 Kb, 8 Kb-9 Kb, and 9 Kb-10 Kb in length. A linker sequence may comprise a length of at least 1 bp, 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 Kb, 2 Kb, 3 Kb, 4 Kb, 5 Kb, 6 Kb, 7 Kb, 8 Kb, 9 Kb, and 10 Kb in length. A linker sequence may comprise a length of at most 1 bp, 2 bp, 3 bp, 4 bp, 5 bp, 6 bp, 7 bp, 8 bp, 9 bp, 10 bp, 20 bp, 30 bp, 40 bp, 50 bp, 60 bp, 70 bp, 80 bp, 90 bp, 100 bp, 200 bp, 300 bp, 400 bp, 500 bp, 600 bp, 700 bp, 800 bp, 900 bp, 1 Kb, 2 Kb, 3 Kb, 4 Kb, 5 Kb, 6 Kb, 7 Kb, 8 Kb, 9 Kb, and 10 Kb in length.

In some aspects, the recombinant virus comprises inverted terminal repeat (ITR) sequences used for packaging the recombinant gene expression cassette into the virion of the viral vector. In some cases, the ITR is from adeno-associated virus (AAV). In some cases, the ITR is from AAV serotype 2.

In some aspects, the recombinant virus and/or plasmid used to generate recombinant virus comprises nucleic acid elements in the following order: a) a first ITR sequence; b) an enhancer sequence; c) a promoter sequence; d) a first exon sequence; e) an intron sequence; f) a second exon sequence; g) a sequence encoding mCoChop; h) a poly A sequence; and i) a second ITR sequence. In some aspects of the recombinant virus and/or plasmid used to generate the recombinant virus, the promoter sequence comprises a promoter/enhancer sequence. In some aspects, the sequence encoding mCoChop comprises a sequence encoding human mCoChop protein or a functional fragment thereof. In other aspects, the plasmid used to generate the recombinant virus further comprises an origin of replication sequence. In some aspects, the plasmid further comprises a sequence for an antibiotic resistance gene.

Pharmaceutical Compositions

A pharmaceutical composition is a formulation containing one or more active ingredients as well as one or more excipients, carriers, stabilizers or bulking agents, which is suitable for administration to a human patient to achieve a desired diagnostic result or therapeutic or prophylactic effect. For storage stability and convenience of handling, a pharmaceutical composition can be formulated as a lyophilized (i.e. freeze dried) or vacuum dried powder which can be reconstituted with saline or water prior to administration to a patient. Alternately, the pharmaceutical composition can be formulated as an aqueous solution. A pharmaceutical composition can contain a proteinaceous active ingredient. Various excipients, such as albumin and gelatin have been used with differing degrees of success to try and stabilize a protein active ingredient present in a pharmaceutical composition. Additionally, cryoprotectants such as alcohols have been used to reduce protein denaturation under the freezing conditions of lyophilization.

Pharmaceutical compositions suitable for internal use include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants such as polysorbates (Tween™), sodium dodecyl sulfate (sodium lauryl sulfate), lauryl dimethyl amine oxide, cetyltrimethylammonium bromide (CTAB), polyethoxylated alcohols, polyoxyethylene sorbitan, octoxynol (Triton X100™), N,N-dimethyldodecylamine-N-oxide, hex adecyltrimethylammonium bromide (HTAB), polyoxyl 10 lauryl ether, Brij 721™, bile salts (sodium deoxycholate, sodium cholate), pluronic acids (F-68, F-127), polyoxyl castor oil (Cremophor™) nonylphenol ethoxylate (Tergitol™), cyclodextrins and, ethylbenzethonium chloride (Hyamine™) Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the internal compositions can be brought about by including in the composition an agent which delays absorption, for example, aluminum monostearate and gelatin.

Sterile solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In one aspect, active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated by reference herein.

The pharmaceutical compositions can be included in a container, pack, or dispenser together with instructions for administration.

Pharmaceutical compositions of the present disclosure comprise, but are not limited to, solutions, emulsions, and liposome-containing formulations. These compositions may be generated from a variety of components that comprise, but are not limited to, preformed liquids, self-emulsifying solids and self-emulsifying semisolids.

Certain compositions of the present disclosure also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The co-administration of a nucleic acid and a carrier compound, generally with an excess of the latter substance, can result in a substantial reduction of the amount of nucleic acid recovered in the liver, kidney or other extra circulatory reservoirs, presumably due to competition between the carrier compound and the nucleic acid for a common receptor. For example, the recovery of a partially phosphorothioate oligonucleotide in hepatic tissue can be reduced when it is co-administered with polyinosinic acid, dextran sulphate, polycytidic acid or 4-acetamido-4'isothiocyano-stilbene-2,2'disulfonic acid (Miyao et al., Antisense Res. Dev., 1995, 5, 115-121; Takakura et al., Antisense & Nucl. Acid Drug Dev., 1996, 6, 177-183).

The vector or recombinant viruses (virions) can be incorporated into pharmaceutical compositions for administration to mammalian patients, particularly humans. The vector or virions can be formulated in nontoxic, inert, pharmaceutically acceptable aqueous carriers, preferably at a pH ranging from 3 to 8, more preferably ranging from 6 to 8, most preferably ranging from 6.8 to 7.2. Such sterile compositions will comprise the vector or virion containing the nucleic acid encoding the therapeutic molecule dissolved in an aqueous buffer having an acceptable pH upon reconstitution.

In some aspects, the pharmaceutical compositions provided herein comprise a therapeutically effective amount of a vector or virion in admixture with a pharmaceutically acceptable carrier and/or excipient, for example saline, phosphate buffered saline, phosphate and amino acids, polymers, polyols, sugar, buffers, preservatives and other proteins. Exemplary amino acids, polymers and sugars and the like are octylphenoxy polyethoxy ethanol compounds, polyethylene glycol monostearate compounds, polyoxyethylene sorbitan fatty acid esters, sucrose, fructose, dextrose, maltose, glucose, mannitol, dextran, sorbitol, inositol, galactitol, xylitol, lactose, trehalose, bovine or human serum albumin, citrate, acetate, Ringer's and Hank's solutions, cysteine, arginine, carnitine, alanine, glycine, lysine, valine, leucine, polyvinylpyrrolidone, polyethylene and glycol. Preferably, this formulation is stable for at least 14 months at −60° C.

In some aspects, the pharmaceutical composition provided herein comprises a buffer, such as phosphate buffered saline (PBS) or sodium phosphate/sodium sulfate, tris buffer, glycine buffer, sterile water and other buffers known to the ordinarily skilled artisan such as those described by Good et al. (1966) Biochemistry 5:467. Preferred pharmaceutical composition contains sodium phosphate, sodium chloride and sorbital. Most preferred pharmaceutical composition contains 10 mM sodium phosphate, 350 mM sodium chloride and 5% (v/v) sorbital. The pH of the buffer in which the pharmaceutical composition comprising the mCoChop contained in the adenoviral vector delivery system, may be in the range of 6.5 to 7.75, 6.5 to 7.5, 6.8 to 7.4 or 6.8 to 7.2.

In some aspects, the pharmaceutical composition provided herein comprises substances which increase the viscosity of the suspension, such as sodium carboxymethyl cellulose, sorbitol, or dextran, in the amount about 1-10 percent, such as 1, 2, 3, 4, 5, 6, 7, 8, 9, or 10 percent (v/v). Preferably the sorbitol is about 3-6% (v/v), most preferably the sorbitol is about 5%. (v/v).

Prior to administration the pharmaceutical composition is free of components used during the production, e.g., culture components, host cell protein, host cell DNA, plasmid DNA and substantially free of mycoplasm, endotoxin, and microbial contamination. Preferably, the pharmaceutical composition has less than 10, 5, 3, 2, or 1 CFU/swab. Most preferably composition has 0 CFU/swab. The endotoxin level in the pharmaceutical composition is less than 20 EU/mL, less than 10 EU/mL or less than 5 EU/mL.

The pharmaceutical composition must have sufficiently full capsid prior to administration. The pharmaceutical composition has at least 50%, at least 60%, at least 70%, at least 80% or greater full capsids.

Kits

Compositions and reagents useful for the present disclosure may be packaged in kits to facilitate application of the present disclosure. In some aspects, the present method provides for a kit comprising a recombinant nucleic acid of the disclosure. In some aspects, the present method provides for a kit comprising a recombinant virus of the disclosure. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose.

In another aspect, the present disclosure provides a kit comprising the pharmaceutical compositions provided herein. In yet another aspect, the disclosure provides kits in the treatment of diseases.

In one aspect, a kit comprises: (a) a recombinant virus provided herein, and (b) instructions to administer to cells or an individual a therapeutically effective amount of the recombinant virus. In some aspects, the kit may comprise pharmaceutically acceptable salts or solutions for administering the recombinant virus. Optionally, the kit can further comprise instructions for suitable operational parameters in the form of a label or a separate insert. For example, the kit may have standard instructions informing a physician or laboratory technician to prepare a dose of recombinant virus.

Optionally, the kit may further comprise a standard or control information so that a patient sample can be compared with the control information standard to determine if the test amount of recombinant virus is a therapeutic amount Optionally, the kit could further comprise devices for administration, such as a syringe, filter needle, extension tubing, cannula, and subretinal injector.

Recombinant viruses may be generated by any suitable means. The methods and compositions and of the disclosure provide for generation of recombinant virus through various means, including the use of transgenic cells, which may include mammalian cells, insect cells, animal cells or fungal cells.

For example, in some aspects, recombinant viruses may be generated through transfection of insect cells via recombinant baculovirus. In some cases, recombinant baculovirus may be generated as an intermediate, whereby the baculovirus may contain sequences necessary for the generation of other viruses such as AAV or rAAV2 viruses. In some cases one or more baculoviruses may be used in the generation of recombinant viruses used for the composition and methods of treatment of this disclosure. In some cases insect cells such as Sf9, High-Five or Sf21 cell lines may be used. In some cases, cell lines may be generated using transient methods (i.e. infection with not stably integrated transgenes). In other cases, cell lines may be generated through the generation of stable cell lines (i.e. infection with transgenes stably integrated into the host cell genome.) In other aspects, the pharmaceutical composition provided herein is manufactured using adherent human embryonic kidney 293 (HEK293) cells. In an alternative aspect, the pharmaceutical composition provided herein is manufactured using suspension-adapted HEK293 cells. In another aspect, the pharmaceutical composition provided herein is manufactured using the baculovirus expression system (BYES) in insect cells. In some aspects, the vector is produced using herpes-helper virus. In some aspects, the vector is produced using producer-clone methods. In some aspects, the vector is produced using Ad-AAV.

Generally, any suitable method may be used in the biochemical purification of recombinant viruses for use in a pharmaceutical composition as described herein. Recombinant viruses may be harvested directly from cells, or from the culture media surrounding host cells. Virus may be purified using various biochemical means, such as gel filtration, filtration, chromatography, affinity purification, gradient ultracentrifugation, or size exclusion methods. Recombinant virus may be tested for content (i.e., identity), purity, or potency (i.e., activity) using any suitable means, before formulation into a pharmaceutical composition. Method may include but are not limited to immunoassays, ELISA, SDS-PAGE, western blot, Northern blot, Southern blot or PCR, HUVEC assays and the like.

Methods of Treatment

The ocular disorders for which the present mCoChop proteins and nucleic acids, and the resulting ChR proteins, are intended and may be used to improve one or more parameters of vision include, but are not limited to, developmental abnormalities that affect both anterior and posterior segments of the eye. Anterior segment disorders include glaucoma, cataracts, corneal dystrophy, keratoconus. Posterior segment disorders include blinding disorders caused by photoreceptor malfunction and/or death caused by retinal dystrophies and degenerations. Retinal disorders include congenital stationary night blindness, macular degeneration such as age-related macular degeneration, congenital cone dystrophies, and a large group of retinitis-pigmentosa (RP)-related disorders. These disorders include genetically predisposed death of photoreceptor cells, rods and cones in the retina, occurring at various ages. Among those are severe retinopathies, such as subtypes of RP itself that progresses with age and causes blindness in childhood and early adulthood and RP-associated diseases, such as genetic subtypes of LCA, which frequently results in loss of vision during childhood, as early as the first year of life. The latter disorders are generally characterized by severe reduction, and often complete loss of photoreceptor cells, rods and cones. (Trabulsi, E I, ed., *Genetic Diseases of the Eye*, Oxford University Press, NY, 1998).

In particular, the mCoChop and ChR proteins of the present invention useful for the treatment and/or restoration of at least partial vision to subjects that have lost vision due to ocular disorders, such as RPE-associated retinopathies, which are characterized by a long-term preservation of ocular tissue structure despite loss of function and by the association between function loss and the defect or absence of a normal gene in the ocular cells of the subject. A variety of such ocular disorders are known, such as childhood onset blinding diseases, retinitis pigmentosa, macular degeneration, and diabetic retinopathy, as well as ocular blinding diseases known in the art. It is anticipated that these other disorders, as well as blinding disorders of presently unknown causation which later are characterized by the same description as above, may also be successfully treated by the CoChop and ChR proteins of the present invention. Thus, the particular ocular disorder treated by the present invention may include the above-mentioned disorders and a number of diseases which have yet to be so characterized.

In particular embodiments, the present disclosure provides a method for treating retinal degenerative diseases, comprising administering a pharmaceutically effective amount of the pharmaceutical compositions provided herein to a subject in need of such treatment. Preferably, the retinal degenerative disease is retinitis pigmentosa or age-related macular degeneration (AMD), wet-AMD, dry-AMD. Additionally, other diseases and disorders that are the direct result of retinal degenerative diseases are also treated by the method of the invention.

In some embodiments, dry AMD may be treated. In some cases, dry AMD may be referred to as central geographic atrophy, characterized by atrophy of the retinal pigment epithelial later below the retina and subsequent loss of photoreceptors in the central part of the eye. The composition and methods of this disclosure provide for the treatment of any and all forms of AMD.

In another aspect, the present disclosure provides a method for prophylactic treatment of AMD or retinitis pigmentosa as described herein, comprising administering a pharmaceutically effective amount of the pharmaceutical compositions provided herein to a human subject in need of such treatment. The present disclosure may be used to treat patients at risk of developing AMD, or presenting early symptoms of the disease. The present disclosure may be used to treat patients at risk of developing MD, or presenting early symptoms of the disease, such as those individuals having a retinal degenerative disease. This may include treatment of eyes either simultaneously or sequentially. Simultaneous treatment may mean that the treatment is administered to each eye at the same time or that both eyes are treated during the same visit to a treating physician or other healthcare provider. It has been documented that patients have a higher risk of developing AMD in a healthy fellow eye of an eye that presents symptoms of AMD, or in patients who have a genetic predisposition toward developing AMD. The present disclosure can be used as a prophylactic treatment in prevention of AMD in the fellow eye.

In some embodiments, mutant CoChop compositions (e.g. nucleotides, polypeptides, cells expressing said polypeptides or containing said nucleotides, pharmaceutical compositions, etc.) disclosed herein are administered to a patient. In some embodiments, mutant CoChop compositions created using the methods ameliorate, or delay the onset of a disease or disorder. In some embodiments, the disease or disorder is a degenerative disease or disorder. In some embodiments, the disease or disorder is an ocular disorder. In some embodiments, the ocular disorder is AMD, macular degeneration or retinitis pigmentosa. In some embodiments, the disease or disorder is injury, brain damage, spinal cord injury, epilepsy, a metabolic disorder, a cardiac dysfunction, vison loss, blindness, deafness, hearing loss or neurological condition. In some embodiments, mutant CoChop compositions disclosed herein are administered to a patient to restore vision loss. In some embodiments, mutant CoChop compositions disclosed herein are administered to a patient to prevent, delay, or ameliorate vision loss.

In some embodiments, the mutant CoChop compositions disclosed herein are administered once to a patient. In some embodiments, the vectors, nucleic acids, or cells disclosed herein are administered about 2 times, about 3 time, about 4 times, about 5 times, about 6 times, about 7 times, about 8 times, about 9 times, about 10 times, about 20 times, about 40 times, or more to a patient. Mutant CoChop compositions disclosed herein are administered until disease or disorder symptoms improve.

In some embodiments, administration of the mutant CoChop compositions disclosed herein improves, prevents, delays, or ameliorates vision loss in a treated patient compared to an untreated patient or the same patient before treatment. In some embodiments, administration of the mutant CoChop compositions disclosed herein improves, prevents, delays, or ameliorates vision loss in a treated patient between day 1 and year 10. In some embodiments, administration of administration of the mutant CoChop compositions disclosed herein improves, prevents, delays, or ameliorates vision loss at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with vision loss in an untreated patient or the same patient before treatment. In some embodiments, administration of the mutant CoChop compositions disclosed herein improves, prevents, delays, or ameliorates vision loss for about 1 day, about 1 week, about 1 month, about 2 months, about 3 months, about 4 months, about 5 months, about 6 months, about 1 year, about 2 years, about 5 years, or about 10 years, or more compared with vision loss in an untreated patient or the same patient before treatment.

In some embodiments, vision loss is decreased by about 1%, about 5%, about 10%, about 20%, about 30%, about 40%, about 50%, about 60%, about 70%, about 80%, about 90%, or about 100% compared with controls or patients treated with other compositions. In some embodiments, administration of the mutant CoChop compositions improves, prevents, ameliorates, or delays vision loss by about 1%, about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with controls or patients treated with other compositions. In some embodiments, administration of the mutant CoChop compositions disclosed herein improves, prevents, ameliorates, or delays vision loss by about 1%, about 5%, about 10%, about 20%, about 30%, about 40%, about 50%, about 60%, about 70%, about 80%, about 90%, or about 100% for about 1, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared with controls or patients treated with other methods.

In some embodiments, administration of the mutant CoChop compositions disclosed herein increases light sensitivity in a treated patient compared to an untreated patient or the same patient before treatment. In some embodiments, administration of the mutant CoChop compositions disclosed herein increases light sensitivity in a treated patient between day 1 and year 10. In some embodiments, administration of administration of the mutant CoChop compositions disclosed herein increases light sensitivity at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with light sensitivity an untreated patient or the same patient before treatment. In some embodiments, administration of the mutant CoChop compositions disclosed herein increases light sensitivity for about 1 day, about 1 week, about 1 month, about 2 months, about 3 months, about 4 months, about 5 months, about 6 months, about 1 year, about 2 years, about 5 years, or about 10 years, or more compared with light sensitivity in an untreated patient or the same patient before treatment.

In some embodiments, light sensitivity is increased by about 1%, about 5%, about 10%, about 20%, about 30%, about 40%, about 50%, about 60%, about 70%, about 80%, about 90%, or about 100% compared with controls or patients treated with other compositions. In some embodiments, administration of the mutant CoChop compositions increases light sensitivity by about 1%, about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with controls or patients treated with other compositions. In some embodiments, administration of the mutant CoChop compositions disclosed herein increases light sensitivity by about 1%, about 5%, about 10%, about 20%, about 30%, about 40%, about 50%, about 60%, about 70%, about 80%, about 90%, or about 100% for about 1, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared with controls or patients treated with other methods.

In some embodiments, administration of the mutant CoChop compositions disclosed herein decreases the light intensity required to elicit a photocurrent in a treated patient compared to an untreated patient or the same patient before treatment. In some embodiments, administration of the mutant CoChop compositions disclosed herein decreases the light intensity required to elicit a photocurrent in a treated patient between day 1 and year 10. In some embodiments, administration of administration of the mutant CoChop compositions disclosed herein decreases the light intensity required to elicit a photocurrent at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with the light intensity required to elicit a photocurrent in an untreated patient or the same patient before treatment. In some embodiments, administration of the mutant CoChop compositions disclosed herein decreases the light intensity required to elicit a photocurrent for about 1 day, about 1 week, about 1 month, about 2 months, about 3 months, about 4 months, about 5 months, about 6 months, about 1 year, about 2 years, about 5 years, or about 10 years, or more compared with the light intensity required to elicit a photocurrent in an untreated patient or the same patient before treatment.

In some embodiments, the light intensity required to elicit a photocurrent is decreased by about 1%, about 5%, about 10%, about 20%, about 30%, about 40%, about 50%, about 60%, about 70%, about 80%, about 90%, or about 100% compared with controls or patients treated with other compositions. In some embodiments, administration of the mutant CoChop compositions decreases the light intensity required to elicit a photocurrent by about 1%, about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with controls or patients treated with other compositions. In some embodiments, administration of the mutant CoChop compositions disclosed herein decreases the light intensity required to elicit a photocurrent by about 1%, about 5%, about 10%, about 20%, about 30%, about 40%, about 50%, about 60%, about 70%, about 80%, about 90%, or about 100% for about 1, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared with controls or patients treated with other methods.

In some embodiments, administration of the mutant CoChop compositions disclosed herein increases ion flux and/or proton flux in a treated patient compared to an untreated patient or the same patient before treatment. In some embodiments, administration of the mutant CoChop compositions disclosed herein increases ion flux and/or proton flux in a treated patient between day 1 and year 10. In some embodiments, administration of administration of the mutant CoChop compositions disclosed herein increases ion flux and/or proton flux at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with ion flux and/or proton flux an untreated patient or the same patient before treatment. In some embodiments, administration of the mutant CoChop compositions disclosed herein increases ion flux and/or proton flux for about 1 day, about 1 week, about 1 month, about 2 months, about 3 months, about 4 months, about 5 months, about 6 months, about 1 year, about 2 years, about 5 years, or about 10 years, or more compared with ion flux and/or proton flux in an untreated patient or the same patient before treatment.

In some embodiments, ion flux and/or proton flux is increased by about 1%, about 5%, about 10%, about 20%, about 30%, about 40%, about 50%, about 60%, about 70%, about 80%, about 90%, or about 100% compared with controls or patients treated with other compositions. In some embodiments, administration of the mutant CoChop compositions increases ion flux and/or proton flux by about 1%, about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with controls or patients treated with other compositions. In some embodiments, administration of the mutant CoChop compositions disclosed herein increases ion flux and/or proton flux by about 1%, about 5%, about 10%, about 20%, about 30%, about 40%, about 50%, about 60%, about 70%, about 80%, about 90%, or about 100% for about 1, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared with controls or patients treated with other methods.

In some embodiments, administration of the mutant CoChop compositions disclosed herein increases visual evoked potential in the visual cortex in a treated patient compared to an untreated patient or the same patient before treatment. In some embodiments, administration of the mutant CoChop compositions disclosed herein increases visual evoked potential in the visual cortex in a treated patient between day 1 and year 10. In some embodiments, administration of administration of the mutant CoChop compositions disclosed herein increases visual evoked potential in the visual cortex at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with the visual evoked potential in the visual cortex in an untreated patient or the same patient before treatment. In some embodiments, administration of the mutant CoChop compositions disclosed herein increases visual evoked potential in the visual cortex for about 1 day, about 1 week, about 1 month, about 2 months, about 3 months, about 4 months, about 5 months, about 6 months, about 1 year, about 2 years, about 5 years, or about 10 years, or more compared with the visual evoked potential in the visual cortex in an untreated patient or the same patient before treatment.

In some embodiments, the visual evoked potential in the visual cortex is increased by about 1%, about 5%, about 10%, about 20%, about 30%, about 40%, about 50%, about 60%, about 70%, about 80%, about 90%, or about 100% compared with controls or patients treated with other compositions. In some embodiments, administration of the mutant CoChop compositions increases visual evoked potential in the visual cortex by about 1%, about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with controls or patients treated with other compositions. In some embodiments, administration of the mutant CoChop compositions disclosed herein increases visual evoked potential in the visual cortex by about 1%, about 5%, about 10%, about 20%, about 30%, about 40%, about 50%, about 60%, about 70%, about 80%, about 90%, or about 100% for about 1, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared with controls or patients treated with other methods.

In some embodiments, administration of the mutant CoChop compositions disclosed herein reduce disease or disorder symptoms in a treated patient compared to an untreated patient or the same patient before treatment. In some embodiments, the disease or disorder symptoms are measured in a treated patient between day 1 and year 10. In some embodiments, administration of the mutant CoChop compositions disclosed herein reduces a disease or disorder symptom at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with the disease or disorder symptom in an untreated patient or the same patient before treatment. In some embodiments, administration of the mutant CoChop compositions disclosed herein reduces a disease or disorder symptom for about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years, or more compared with the disease or disorder symptom in an untreated patient or the same patient before treatment.

In some embodiments, the disease or disorder symptom is reduced by about 1%, about 5%, about 10%, about 20%, about 30%, about 40%, about 50%, about 60%, about 70%, about 80%, about 90%, or about 100% compared with the disease or disorder symptom in an untreated patient or the same patient before treatment. In some embodiments, administration of the mutant CoChop compositions disclosed herein reduces the disease or disorder symptom by about 1%, about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with the disease or disorder symptom in an untreated patient or the same patient before treatment. In some embodiments, administration of the mutant CoChop compositions disclosed herein reduces the disease or disorder symptom by about 1%, about 5%, about 10%, about 20%, about 30%, about 40%, about 50%, about 60%, about 70%, about 80%, about 90%, or about 100% for about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared with the disease or disorder symptom in an untreated patient or the same patient before treatment.

In some embodiments, administration of the mutant CoChop compositions disclosed herein reduce symptoms of AMD in a treated patient compared to an untreated patient or the same patient before treatment. In some embodiments, the symptom is blurred vision, decrease in visual acuity, partial loss of vision, and/or an inability to see in dim light. In some embodiments, the AMD symptoms are measured in a treated patient between day 1 and year 10. In some embodiments, administration of the mutant CoChop compositions disclosed herein reduces an AMD symptom at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with the AMD symptom in an untreated patient or the same patient before treatment. In some embodiments, administration of the mutant CoChop compositions disclosed herein reduces an AMD symptom for about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years, or more compared with the AMD symptom in an untreated patient or the same patient before treatment.

In some embodiments, the AMD symptom is reduced by about 1%, about 5%, about 10%, about 20%, about 30%, about 40%, about 50%, about 60%, about 70%, about 80%, about 90%, or about 100% compared with the AMD symptom in an untreated patient or the same patient before treatment. In some embodiments, administration of the mutant CoChop compositions disclosed herein reduces the AMD symptom by about 1%, about 5%, about 10%, about 20%, about 30%, about 40%, about 50%, about 60%, about 70%, about 80%, about 90%, or about 100% at about day 1, about day 2, about day 3, about day 4, about day 5, about day 6, about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with the AMD symptom in an untreated patient or the same patient before treatment. In some embodiments, administration of the mutant CoChop compositions disclosed herein reduces the AMD symptom by about 1%, about 5%, about 10%, about 20%, about 30%, about 40%, about 50%, about 60%, about 70%, about 80%, about 90%, or about 100% for about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 1 year, about 2 years, about 5 years, or about 10 years or more compared with the AMD symptom in an untreated patient or the same patient before treatment.

The term "subject," or "individual" or "patient" as used herein in reference to individuals having a disease or disorder or are suspected of having a disease or disorder, and the like. Subject, individual or patent may be used interchangeably in the disclosure and encompass mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some aspects of the methods and compositions provided herein, the mammal is a human.

Efficacy of the treatment will be established for example by evaluating the best corrected visual acuity of each eye. Visual acuity test are performed using the Electronic visual acuity (EVA) ETDRS (Early Treatment for Diabetic Retinopathy Study) methodology, or low vision assessment of hand motion and light perception.

The term "vision" as used herein is defined as the ability of an organism to usefully detect light as a stimulus for differentiation or action. Vision is intended to encompass the following:
1. Light detection or perception—the ability to discern whether or not light is present;
2. Light projection—the ability to discern the direction from which a light stimulus is coming;
3. Resolution—the ability to detect differing brightness levels (i.e., contrast) in a grating or letter target; and
4. Recognition—the ability to recognize the shape of a visual target by reference to the differing contrast levels within the target.

Thus, "vision" includes the ability to simply detect the presence of light. The polypeptides and polynucleotides encoding mutant CoChop of the present invention can be used to improve or restore vision, wherein the improvement or restoration in vision includes, for example, increases in light detection or perception, increase in light sensitivity or photosensitivity in response to a light stimulus, increase in the ability to discern the direction from which a light stimulus is coming, increase in the ability to detect differing brightness levels, increase in the ability to recognize the shape of a visual target, and increases in visual evoked potential or transmission from the retina to the cortex. As such, improvement or restoration of vision may or may not include full restoration of sight, i.e., wherein the vision of the patient treated with the present invention is restored to the degree to the vision of a non-affected individual. The visual recovery described in the animal studies described below may, in human terms, place the person on the low end of vision function by increasing one aspect of vision (i.e., light sensitivity, or visual evoked potential) without restoring full sight. Nevertheless, placement at such a level would be a significant benefit because these individuals could be trained in mobility and potentially in low order resolution tasks which would provide them with a greatly improved level of visual independence compared to total blindness. Even basic light perception can be used by visually impaired individuals, whose vision is improved using the present compositions and methods, to accomplish specific daily tasks and improve general mobility, capability, and quality of life.

The degree of restoration of vision can be determined through the measurement of vision before, and preferably after, administering a vector comprising, for example, DNA encoding CoChop. Vision can be measured using any of a number of methods well-known in the art or methods not yet established. Vision, as improved or restored by the present invention, can be measured by any of the following visual responses:
1. a light detection response by the subject after exposure to a light stimulus—in which evidence is sought for a reliable response of an indication or movement in the general direction of the light by the subject individual when the light it is turned on;
2. a light projection response by the subject after exposure to a light stimulus in which evidence is sought for a reliable response of indication or movement in the specific direction of the light by the individual when the light is turned on;
3. light resolution by the subject of a light vs. dark patterned visual stimulus, which measures the subject's capability of resolving light vs dark patterned visual stimuli as evidenced by:
   a. the presence of demonstrable reliable optokinetically produced nystagmoid eye movements and/or related head or body movements that demonstrate tracking of the target (see above) and/or b. the presence of a reliable ability to discriminate a pattern visual stimulus and to indicate such discrimination by verbal or non-verbal means, including, for example pointing, or pressing a bar or a button; or 4. electrical recording of a visual cortex response to a light flash stimulus or a pattern visual stimulus, which is an endpoint of electrical transmission from a restored retina to the visual cortex, also referred to as the visual evoked potential (VEP). Measurement may be by electrical recording on the scalp surface at the region of the visual cortex, on the cortical surface, and/or recording within cells of the visual cortex.

Thus, improvement or restoration of vision, according to the present invention, can include, but is not limited to: increases in amplitude or kinetics of photocurents or electrical response in response to light stimulus in the retinal cells, increases in light sensitivity (i.e., lowering the threshold light intensity required for initiating a photocurrent or electrical response in response to light stimulus, thereby requiring less or lower light to evoke a photocurrent) of the retinal cells, increases in number or amplitude of light-evoked spiking or spike firings, increases in light responses to the visual cortex, which includes increasing in visual evoked potential transmitted from the retina or retinal cells to the visual cortex or the brain.

Both in vitro and in vivo studies to assess the various parameters of the present invention may be used, including recognized animal models of blinding human ocular disorders. Large animal models of human retinopathy, e.g., childhood blindness, are useful. The examples provided herein allow one of skill in the art to readily anticipate that this method may be similarly used in treating a range of retinal diseases.

While earlier studies by others have demonstrated that retinal degeneration can be retarded by gene therapy techniques, the present invention demonstrates a definite physiological recovery of function, which is expected to generate or improve various parameters of vision, including behavioral parameters.

Behavioral measures can be obtained using known animal models and tests, for example performance in a water maze, wherein a subject in whom vision has been preserved or restored to varying extents will swim toward light (Hayes, J M et al., 1993, *Behav Genet* 23:395-403).

In models in which blindness is induced during adult life or congenital blindness develops slowly enough that the individual experiences vision before losing it, training of the subject in various tests may be done. In this way, when these tests are re-administered after visual loss to test the efficacy of the present compositions and methods for their vision-restorative effects, animals do not have to learn the tasks de novo while in a blind state. Other behavioral tests do not require learning and rely on the instinctiveness of certain behaviors. An example is the optokinetic nystagmus test (Balkema G W et al., 1984, *Invest Ophthalmol Vis Sci.* 25:795-800; Mitchiner J C et al., 1976, *Vision Res.* 16:1169-71).

The present invention may also be used in combination with other forms of vision therapy known in the art to improve or restore vision. For example, the use of visual prostheses, which include retinal implants, cortical implants, lateral geniculate nucleus implants, or optic nerve implants. Thus, in addition to genetic modification of surviving retinal neurons using the present methods, the subject being treated may be provided with a visual prosthesis before, at the same time as, or after the molecular method is employed. The effectiveness of visual prosthetics can be improved with training of the individual, thus enhancing the potential impact of the CoChop transformation of patient cells as contemplated herein. Training methods, such as habituation training characterized by training the subject to recognize recognize (i) varying levels of light and/or pattern stimulation, and/or (ii) environmental stimulation from a common light source or object as would be understood by one skilled in the art; and orientation and mobility training characterized by training the subject to detect visually local objects and move among said objects more effectively than without the training. In fact, any visual stimulation techniques that are typically used in the field of low vision rehabilitation are applicable here.

In some embodiments, use of different opsin genes in addition to the mutant CoChop proteins of the present invention and targeted gene expression may further increase light sensitivity or improve vision. Visual information is processed through the retina through two pathways: an ON pathway which signals the light ON, and an OFF pathway which signals the light OFF. The existence of the ON and OFF pathway is important for the enhancement of contrast sensitivity. The visual signal in the ON pathway is relay from ON-cone bipolar cells to ON ganglion cells. Both ON-cone bipolar cells and ON-ganglion cells are depolarized in response to light. On the other hand, the visual signal in the OFF pathway is carried from OFF-cone bipolar cells to OFF ganglion cells. Both OFF-cone bipolar cells and OFF-ganglion cells are hypopolarized in response to light. Rod bipolar cells, which are responsible for the ability to see in dim light (scotopic vision), are ON bipolar cells (depolarized in response to light). Rod bipolar cells relay the vision signal through AII amacrine cells (an ON type retinal cells) to ON an OFF cone bipolar cells.

Accordingly, a dual rhodopsin system can be used to recapitulate the ON and OFF pathways integral to visual processing and acuity. Briefly, a CoChop protein of the present invention can be specifically targeted to ON type retinal neurons (i.e., ON type ganglion cells and/or ON type bipolar cells), while a hypopolarizing light sensor (i.e., halorhodopsin or other chloride pump known in the art) can be targeted to OFF type retinal neurons (i.e. OFF type ganglion cells and/or OFF type bipolar cells) to create ON and OFF pathways. The specific targeting to preferred cell subpopulations can be achieved through the use of different cell type-specific promoters. For example, CoChop expression may be driven by the mGluR6 promoter for targeted expression in ON-type retinal neurons (i.e., ON type ganglion cells and/or ON type bipolar cells) while a hypopolarizing channel, such as halorhodopsin, expression is driven by the NK-3 promoter for targeted expression in OFF-type retinal neurons (i.e., OFF type ganglion cells and/or OFF type bipolar cells).

An alternative approach to restore ON and OFF pathways in the retina is achieved by, expressing a depolarizing light sensor, to rod bipolar cells or AII amacrine. In this approach, the depolarization of rod bipolar cells or AII amacrine cells can lead to the ON and OFF responses at the levels of cone bipolar cells and the downstream retinal ganglion cells. Thus, the ON and OFF pathways that are inherent in the retina are maintained.

Method of Delivery

In some aspects, the pharmaceutical composition is administered by any method known in the art to treat or prevent a particular disease or disorder. In preferred embodiments, when treating ocular disorders the pharmaceutical composition is administered to intravitreal sites using any direction method. In some cases, the delivery method may be by injection, such as those described in US Pat Pub. No. 2010008170, which is incorporated by reference in its entirety. In some cases, direct administration to the vitreous includes injection of a liquid pharmaceutical composition via syringe. In another example, direct administration may involve injection via a cannula or other suitable instrument for delivery for a vector or recombinant virus. In other examples, direct administration may comprise an implant further comprising a suitable vector for delivery of transgenes such as mCoChop. In some cases the implant may be either directly implanted in or near the retina.

Generally, the vector can be delivered in the form of a suspension injected intraocularly (intravitreally). Specifically, the vector is injected transclerally through the pars plana.

Definitions

The compositions and methods of this disclosure as described herein may employ, unless otherwise indicated, conventional techniques and descriptions of molecular biology (including recombinant techniques), cell biology, biochemistry, immunochemistry and ophthalmic techniques, which are within the skill of those who practice in the art. Such conventional techniques include methods for observing and analyzing the retina, or vision in a subject, cloning and propagation of recombinant virus, formulation of a pharmaceutical composition, and biochemical purification and immunochemistry. Specific illustrations of suitable techniques can be had by reference to the examples herein. However, equivalent conventional procedures can, of course, also be used. Such conventional techniques and descriptions can be found in standard laboratory manuals such as Green, et al., Eds., Genome Analysis: A Laboratory Manual Series (Vols. I-IV) (1999); Weiner, et al., Eds., Genetic Variation: A Laboratory Manual (2007); Dieffenbach, Dveksler, Eds., PCR Primer: A Laboratory Manual (2003); Bowtell and Sambrook, DNA Microarrays: A Molecular Cloning Manual (2003); Mount, Bioinformatics: Sequence and Genome Analysis (2004); Sambrook and Russell, Condensed Protocols from Molecular Cloning: A Laboratory Manual (2006); and Sambrook and Russell, Molecular Cloning: A Laboratory Manual (2002) (all from Cold Spring Harbor Laboratory Press); Stryer, L., Biochemistry (4th Ed.) W.H. Freeman, N.Y. (1995); Gait, "Oligonucleotide Synthesis: A Practical Approach" IRL Press, London (1984); Nelson and Cox, Lehninger, Principles of Biochemistry, 3rd Ed., W.H. Freeman Pub., New York (2000); and Berg et al., Biochemistry, 5th Ed., W.H. Freeman Pub., New York (2002), all of which are herein incorporated by reference in their entirety for all purposes.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

Ranges can be expressed herein as from "about" one particular value, and/or to "about" another particular value. When such a range is expressed, another case includes from the one particular value and/or to the other particular value. Similarly, when values are expressed as approximations, by use of the antecedent "about," it will be understood that the particular value forms another case. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5. The term "about" also accounts for typical error or imprecision in measurement of values.

The term "retinal degenerative diseases" encompasses all diseases associated with photoreceptor degeneration. Retinal degenerative diseases include but are not limited to Retinitis Pigmentosa, age-related macular degeneration, Bardet-Biedel syndrome, Bassen-Kornzweig syndrome, Best disease, choroideremia, gyrate atrophy, Leber congenital amaurosis, Refsun syndrome, Stargardt disease or Usher syndrome.

In the context of the invention, the term "treating" or "treatment", as used herein, means reversing, alleviating, inhibiting the progress of, or preventing the disorder or condition to which such term applies, or one or more symptoms of such disorder or condition (e.g., retinal degenerative diseases).

According to the invention, the term "patient" or "patient in need thereof", is intended for a human or non-human mammal affected or likely to be affected with a retinal degenerative disease.

As intended herein the expression "isolated nucleic acid" refers to any type of isolated nucleic acid, it can notably be natural or synthetic, DNA or RNA, single or double stranded. In particular, where the nucleic acid is synthetic, it can comprise non-natural modifications of the bases or bonds, in particular for increasing the resistance to degradation of the nucleic acid. Where the nucleic acid is RNA, the modifications notably encompass capping its ends or modifying the 2' position of the ribose backbone so as to decrease the reactivity of the hydroxyl moiety, for instance by suppressing the hydroxyl moiety (to yield a 2'-deoxyribose or a 2'-deoxyribose-2'-fluororibose), or substituting the hydroxyl moiety with an alkyl group, such as a methyl group (to yield a 2'-O-methyl-ribose).

The term "channelrhodopsin" refers to the subfamily of retinylidene proteins (rhodopsins) that function as light-gated ion channels. Some serve as sensory photoreceptors in unicellular green algae, controlling phototaxis: movement in response to light. Expressed in cells of other organisms, they enable light to control electrical excitability, intracellular acidity, calcium influx, and other cellular processes. They are larger than many other rhodopsins, with a 7 transmembrane (7TM) region and a long C-terminal extension. In algae they function as visual proteins directing the alga towards or away from a light source and to find light conditions that are optimal for photosynthetic growth. The 7TM region shows some homology to other microbial (procaryotic) rhodopsins functioning as light-driven pumps (bacteriorhodopsin, archeorhodopsin and halorhodopsin) or sensors. Term also include polypeptides that are homologous to channelrhodopsin.

Two amino acid sequences or nucleic acid sequences are "substantially homologous" or "substantially similar" when greater than 80%, preferably greater than 85%, preferably greater than 90% of the amino acids or nucleic acid sequences are identical, or greater than about 90%, preferably greater than 95%, are similar (functionally identical). To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences. In one embodiment, the two sequences are the same length. The determination of percent identity between two sequences can be accomplished using a mathematical algorithm. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference in their entireties. All published foreign patents and patent applications cited herein are hereby incorporated by reference in their entireties. All other published references, documents, manuscripts and scientific literature cited herein are hereby incorporated by reference in their entireties.

While this invention has been particularly shown and described with references to preferred embodiments thereof, it will be understood by those skilled in the art that various changes in form and details may be made therein without departing from the scope of the invention encompassed by the appended claims.

This disclosure is further illustrated by the following non-limiting examples.

EXAMPLES

Example 1—Creation and Analysis of Mutant CoChop Polypeptides

Figure 6:
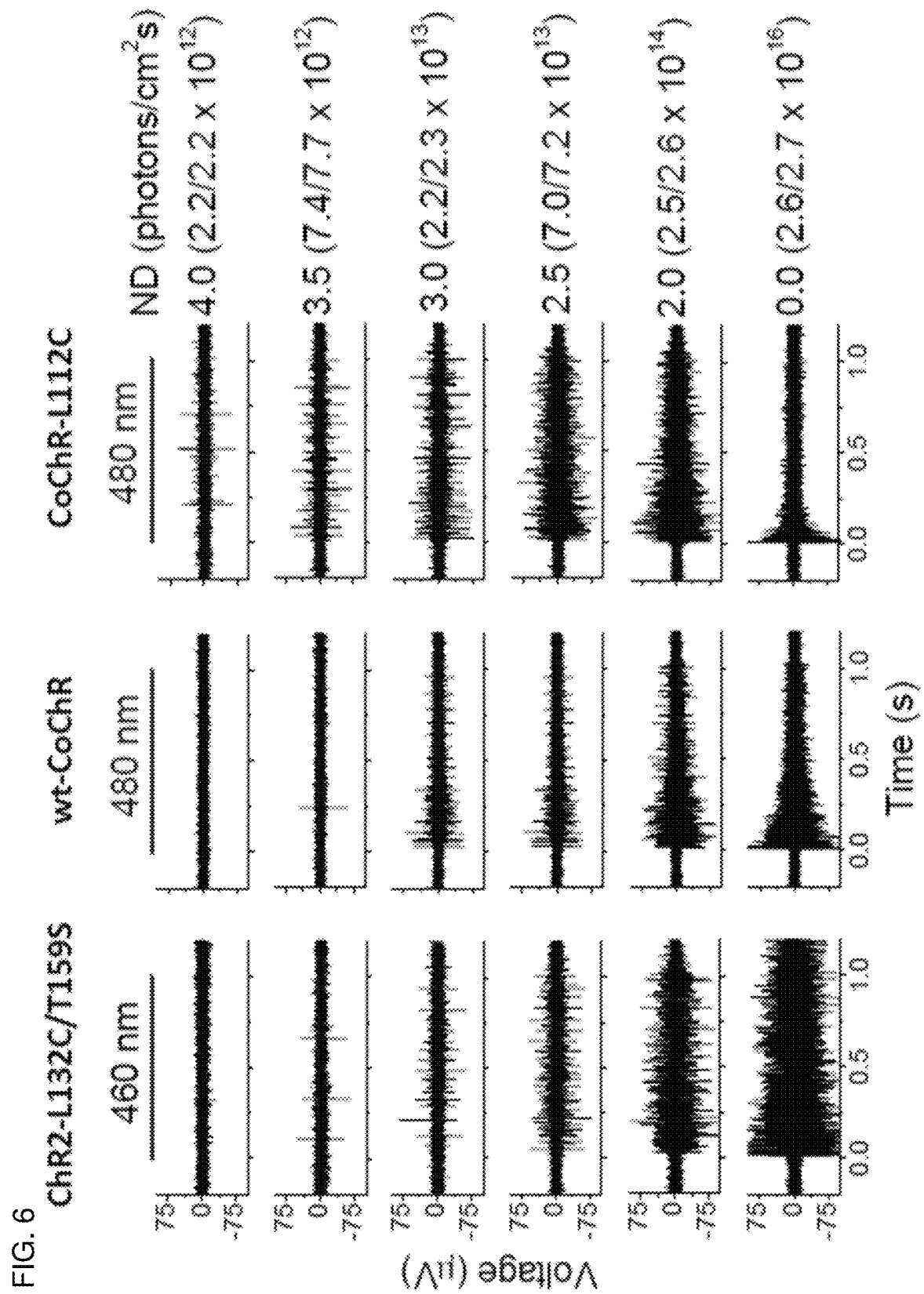
FIG. 6: Comparison of the light sensitivities of ChR2-L132C/T159C, wt-CoChR, and CoChR-L112C in retinal ganglion cells with multi-electrode array recordings. The light intensities are shown in neutral density (ND) and photons/cm$^2$s.
Figure 7:
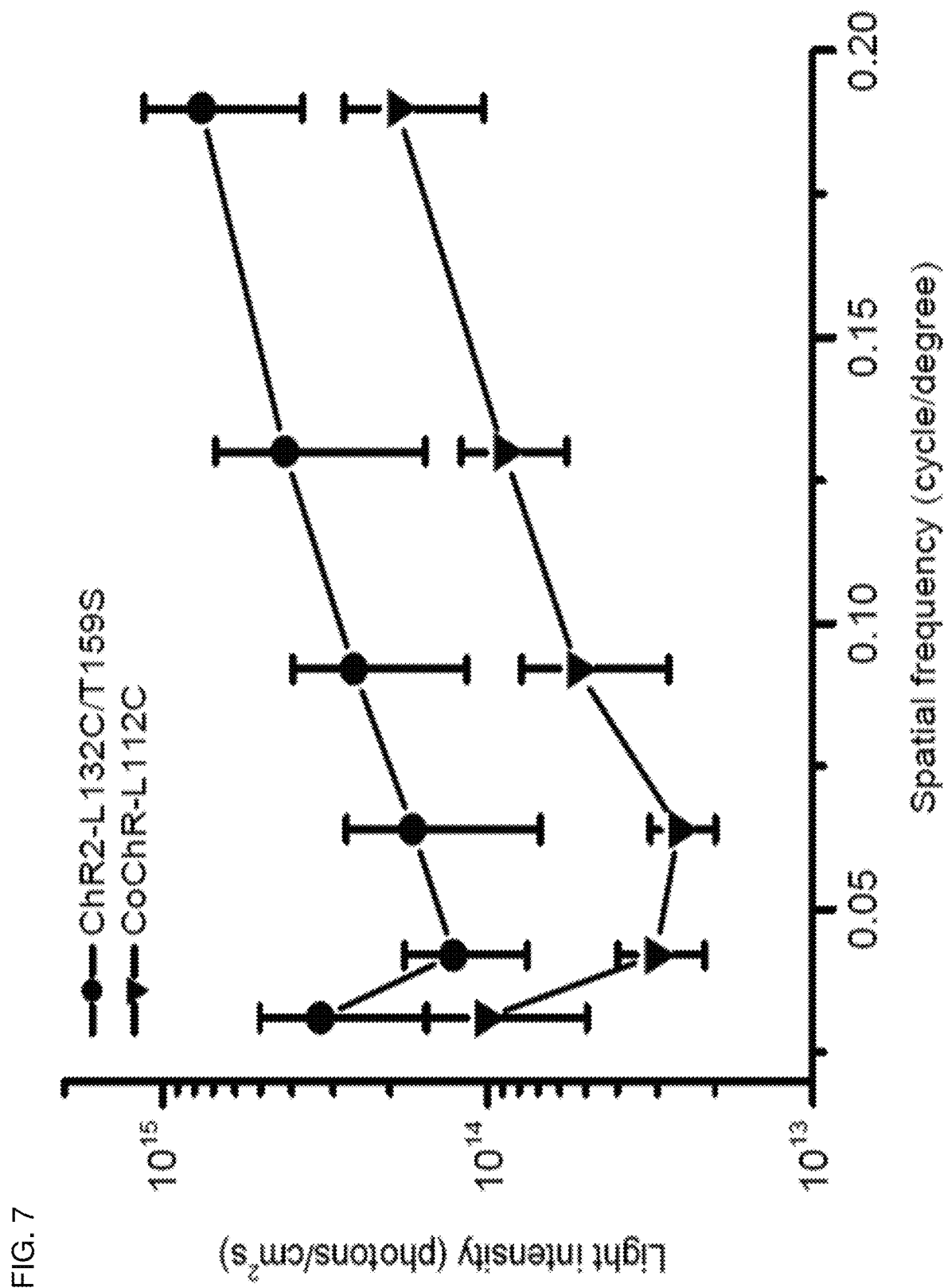
FIG. 7: Optomotor behavioral tests for the comparison of the light sensitivity of the restored optomotor responses between ChR2-L132C/T159S and CoChR-L112C virus vector injected mice. The relationship of spectral frequency and threshold light intensity required to evoke optomotor response for ChR2-L132C/T159S and CoChR-L112C. The experiments were carried out using a blind mouse line. Optomotor tests were conducted in a home-made optomotor assay system. The light stimulus was generated by blue LED with the wavelength of ~470 nm. The threshold light intensity to evoke optomotor response for CoChR-L112C-expressing mice was around at $2-3 \times 10^{13}$ photons/cm$^2$s and for ChR2-L132C/T159S-expressing mice was around at $1-2 \times 10^{14}$ photons/cm$^2$s. Data are shown as the mean±SD.
Figure 8:
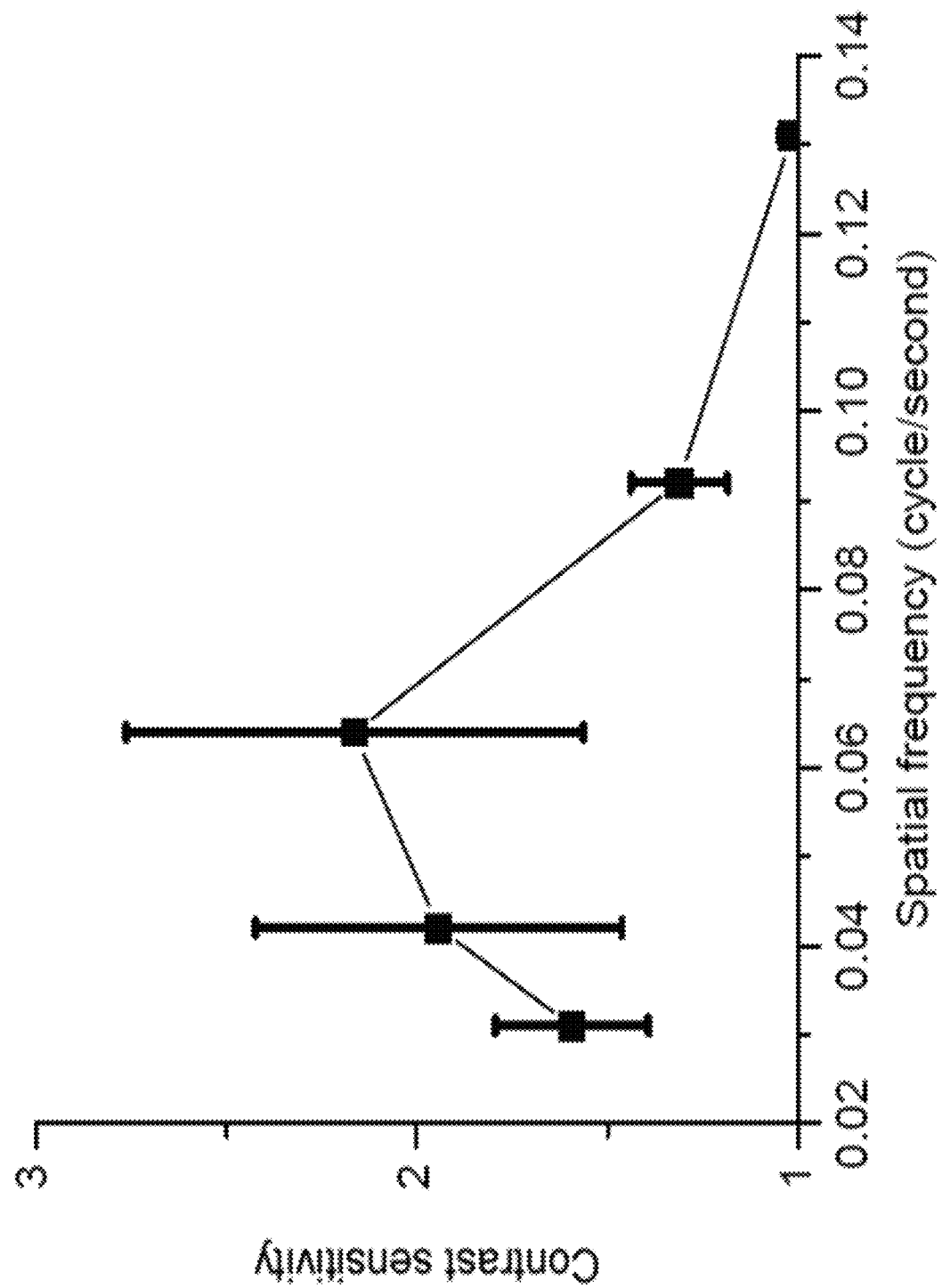
FIG. 8: Contrast sensitivity curve for the CoChR-L112C virus vector injected mice based on optomotor behavioral tests. Experiments were carried out using a blind mouse line. Optomotor tests were conducted in a virtual optomotor system (OptoMotry; CerebralMechanics, Lethbridge, AB, Canada). The illuminance inside the platform was ~150 lux. Data are shown as the mean±SD.
Figure 9A:
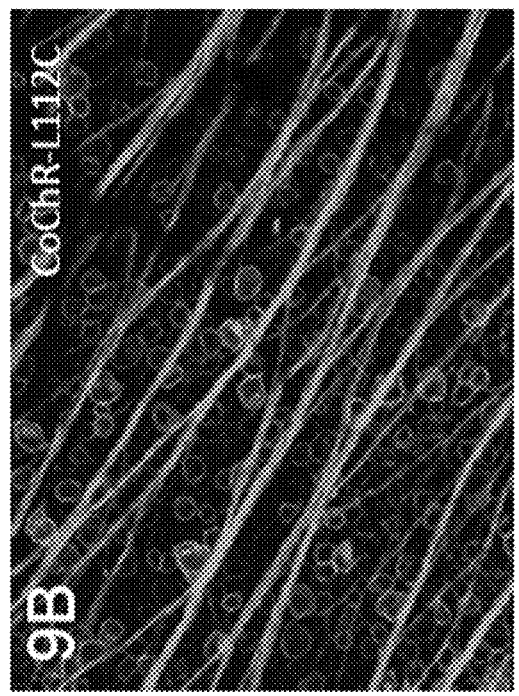
FIGS. 9A-9G: Long-term stable expression of wt-CoChR and CoChR-L112C in retinal neurons mediated thought AAV vector delivery. Fluorescence images show the expression wt-CoChR (FIG. 9A) and its mutant CoChR-L112C (FIG. 9B) in retinal ganglion cells in C57BL/6J mice one month after virus injection. Fluorescence images show the expression wt-CoChR (FIG. 9C) and its mutant CoChR-L112C (FIG. 9D) in retinal ganglion cells in rd1 mice six months after virus injection. Fluorescence images show the expression CoChR-L112C in the retina of a blind mouse line viewed in whole-mount at low (FIG. 9E) and high (FIG. 9F) magnification and in retinal vertical section (FIG. 9G) nine months after virus injection.
Figure 9B:
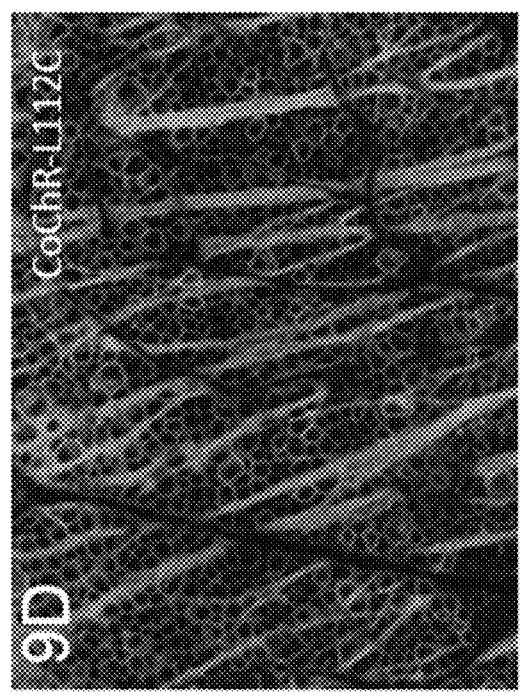
Figure 9C:
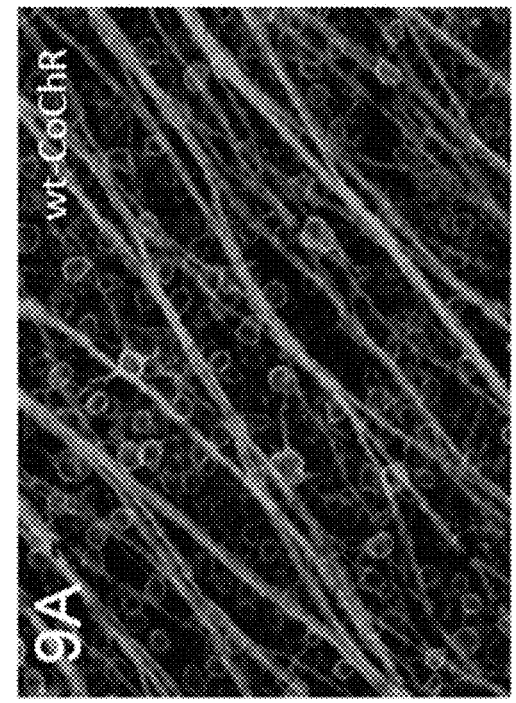
Figure 9D:
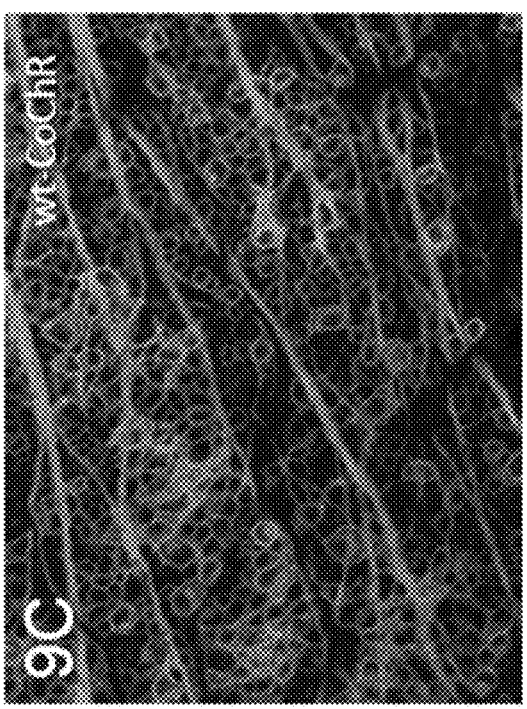
Figure 9F:
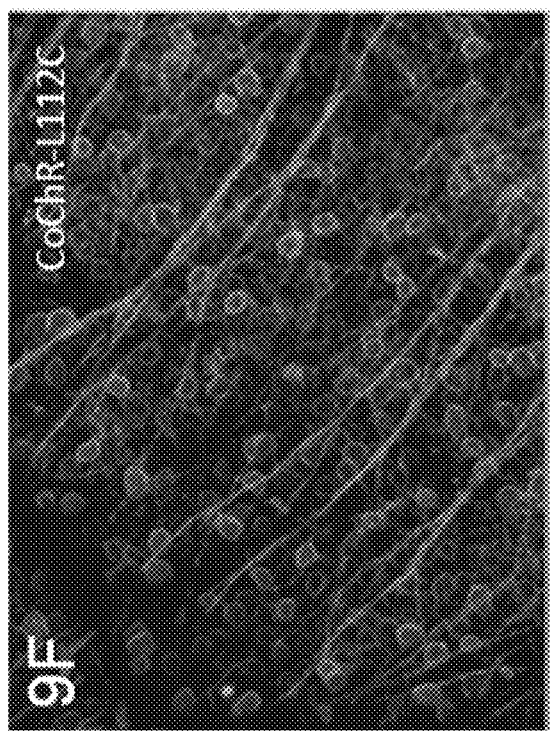
Figure 9G:
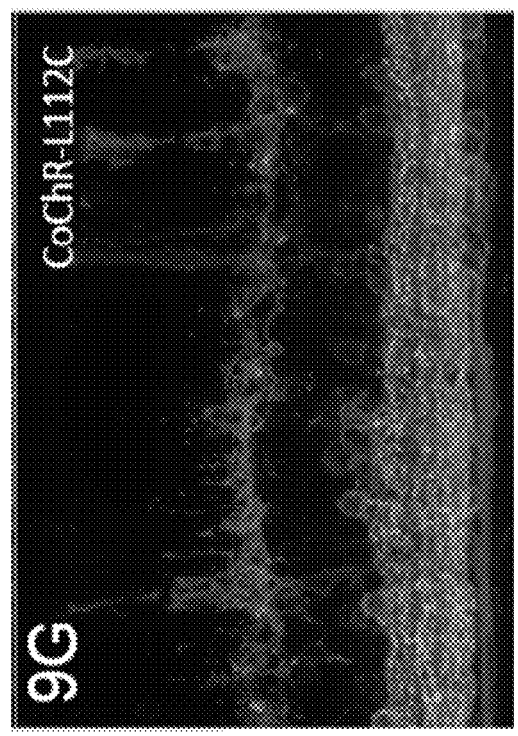
Figure 9E:
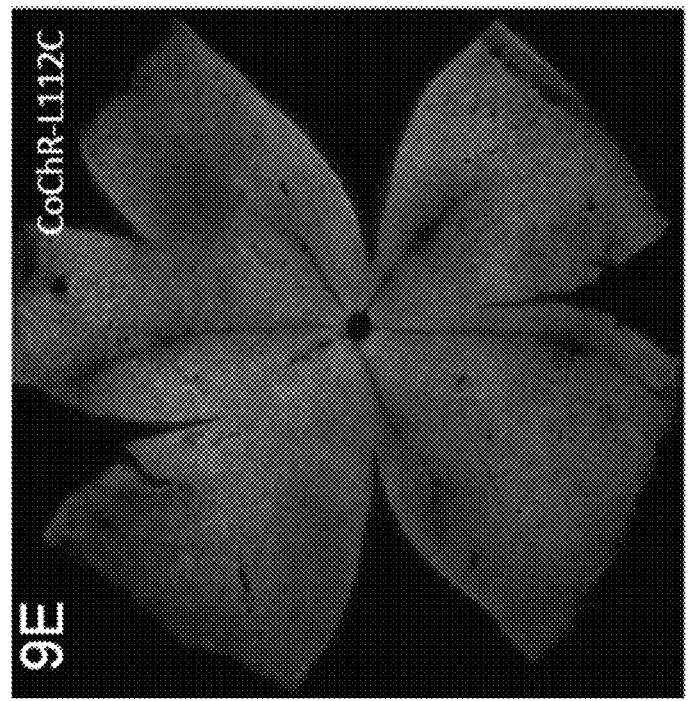

Channelrhodopsons (ChRs), such ChR2, are promising optogenetic light sensors for vision restoration. A major obstacle for using ChR2 in vision restoration is its low light sensitivity. We previously made more light-sensitive ChR2s by optimizing its kinetics through site-direct mutagenesis, including the most light-sensitive ChR2 mutant, ChR2-L132C/T159S. Recently, a number of ChR variants have been reported by de novo transcriptome sequencing of algae (Klapoetke et al., 2014 Nat. Methods 11(3): 338-46). We found that one of the variants, CoChR, displayed large photocurrent. In this invention, we made several highly light-sensitive CoChR mutants (i.e. mutant CoChop) by optimizing its kinetics through site-direct mutagenesis. These mutants include CoChR-L112C (SEQ ID NO: 3), CoChR-T139C (SEQ ID NO: 5), C68S/V69I (SEQ ID NO: 4), C68T/V69I (SEQ ID NO: 7), CoChR-T145A/S146A (SEQ ID NO: 6), CoChR-L112C/T139C (SEQ ID NO: 8), CoChR-L112C/H94E (SEQ ID NO: 9), and CoChR-L112C/H94E/K264T (SEQ ID NO: 10). CoChR and its mutants exhibit a slight red-shifted spectral curve than that of ChR2 with a peak spectrum at 480 nm (FIG. 1). The light sensitivity of CoChR mutants (as shown for CoChR-L112C) are much higher than that of the most light-sensitive ChR2 mutant, ChR2-L132C/T159S, based on electrophysiology recordings in HEK cells (FIGS. 2-5) and multi-electrode array recordings from retinal neurons (FIG. 6), and optomotor behavioral tests from blind mice in vivo (FIG. 7). Furthermore, optomotor response can be observed for CoChR-L112C-expressing mice under ambient light conditions (FIG. 8). In addition, long-term stable expression of CoChR-L112C mutant was observed in retinal neurons (FIGS. 9A-9G).

What is claimed is:

1. A method of treating an ocular disease or disorder treatable by restoring light sensitivity to retinal neurons, the method comprising administering to a subject a therapeutically effective amount of a pharmaceutical composition comprising a nucleic acid encoding a polypeptide comprising the amino acid sequence of any one of SEQ ID NOs: 3-10, wherein the nucleic acid is operably linked to a promoter and the polypeptide is expressed in a cell membrane of a retinal neuron of the subject following administration.

2. The method of claim 1, wherein the nucleic acid is incorporated into a recombinant adeno-associated virus (rAAV) viral vector.

3. The method of claim 2, wherein the rAAV viral vector is a recombinant form of an adeno-associated virus (AAV) selected from the group consisting of AAV1, AAV2, AAV2.5, AAV3, AAV4, AAV5, AAV6, AAV7, AAV8, AAV9, AAV10, AAV11, AAV12, and rh10.

4. The method of claim 3, wherein the AAV is AAV2.

5. The method of claim 1, wherein the ocular disease or disorder is congenital cone dystrophies, or retinitis pigmentosa (RP).

6. The method of claim 1, wherein the ocular disease or disorder is retinitis pigmentosa or diabetic retinopathy.

7. The method of claim 1, wherein said restoring light sensitivity comprises any one or more of increasing light sensitivity, lowering a threshold light intensity required to elicit a photocurrent, increasing ion flux and/or proton flux, or increasing visual evoked potential in the visual cortex.

8. The method of claim 1, wherein the pharmaceutical composition is administered to an eye of the subject by intravitreal injection, subretinal injection, injection via a cannula, or an implant.

9. The method of claim 8, wherein the pharmaceutical composition is administered to an eye of the subject by intravitreal or subretinal injection.

10. The method of claim 1, wherein the subject is a human.

11. A method of improving light sensitivity in an eye of a subject, the method comprising administering to the subject a therapeutically effective amount of a pharmaceutical composition comprising a nucleic acid encoding a polypeptide comprising the amino acid sequence of any one of SEQ ID NOs: 3-10, wherein the nucleic acid is operably linked to a promoter and the polypeptide is expressed in a cell membrane of a cell in the eye of the subject following administration.

* * * * *

SEQUENCE LISTING

```
<160> NUMBER OF SEQ ID NOS: 10

<210> SEQ ID NO 1
<211> LENGTH: 864
<212> TYPE: DNA
<213> ORGANISM: Artificial Sequence
<220> FEATURE:
<223> OTHER INFORMATION: synthetic sequence

<400> SEQUENCE: 1
atgctgggaa acggcagcgc cattgtgcct atcgaccagt gcttttgcct ggcttggacc      60
gacagcctgg gaagcgatac agagcagctg gtggccaaca tcctccagtg gttcgccttc     120
ggcttcagca tcctgatcct gatgttctac gcctaccaga cttggagagc cacttgcggt     180
```

```
tgggaggagg tctacgtctg ttgcgtcgag ctgaccaagg tcatcatcga gttcttccac    240
gagttcgacg accccagcat gctgtacctg gctaacggac accgagtcca gtggctgaga    300
tacgcagagt ggctgctgac ttgtcccgtc atcctgatcc acctgagcaa cctgacaggc    360
ctgaaggacg actacagcaa gcggaccatg aggctgctgg tgtcagacgt gggaaccatc    420
gtgtggggag ctacaagcgc catgagcaca ggctacgtca aggtcatctt cttcgtgctg    480
ggttgcatct acggcgccaa caccttcttc acgccgcca agtgtatat cgagagctac     540 cacgtggtgc caaagggcag acctagaacc gtcgtgcgga tcatggcttg gctgttcttc    600
ctgtcttggg gcatgttccc cgtgctgttc gtcgtgggac cagaaggatt cgacgccatc    660
agcgtgtacg gctctaccat tggccacacc atcatcgacc tcatgagcaa gaattgttgg    720
ggcctgctgg acactatct gagagtgctg atccaccagc acatcatcat ctacggcgac     780
atccgcaaga agaccaagat caacgtggcc ggcgaggaga tggaagtgga gaccatggtg    840
gaccaggagg acgaggagac agtg                                          864
```

```
<210> SEQ ID NO 2
<211> LENGTH: 288
<212> TYPE: PRT
<213> ORGANISM: Artificial Sequence
<220> FEATURE:
<223> OTHER INFORMATION: synthetic sequence

<400> SEQUENCE: 2

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30

Asn Ile Leu Gln Trp Phe Ala Phe Gly Phe Ser Ile Leu Ile Leu Met
        35                  40                  45

Phe Tyr Ala Tyr Gln Thr Trp Arg Ala Thr Cys Gly Trp Glu Glu Val
    50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly His Arg Val
                85                  90                  95

Gln Trp Leu Arg Tyr Ala Glu Trp Leu Leu Thr Cys Pro Val Ile Leu
            100                 105                 110

Ile His Leu Ser Asn Leu Thr Gly Leu Lys Asp Asp Tyr Ser Lys Arg
        115                 120                 125

Thr Met Arg Leu Leu Val Ser Asp Val Gly Thr Ile Val Trp Gly Ala
    130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
    210                 215                 220

Ser Thr Ile Gly His Thr Ile Ile Asp Leu Met Ser Lys Asn Cys Trp
225                 230                 235                 240
```

```
Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
                260                 265                 270

Glu Met Glu Val Glu Thr Met Val Asp Gln Glu Asp Glu Glu Thr Val
                275                 280                 285

<210> SEQ ID NO 3
<211> LENGTH: 288
<212> TYPE: PRT
<213> ORGANISM: Artificial
<220> FEATURE:
<223> OTHER INFORMATION: synthetic sequence

<400> SEQUENCE: 3

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
                20                  25                  30

Asn Ile Leu Gln Trp Phe Ala Phe Gly Phe Ser Ile Leu Ile Leu Met
                35                  40                  45

Phe Tyr Ala Tyr Gln Thr Trp Arg Ala Thr Cys Gly Trp Glu Glu Val
    50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly His Arg Val
                85                  90                  95

Gln Trp Leu Arg Tyr Ala Glu Trp Leu Leu Thr Cys Pro Val Ile Cys
                100                 105                 110

Ile His Leu Ser Asn Leu Thr Gly Leu Lys Asp Asp Tyr Ser Lys Arg
                115                 120                 125

Thr Met Arg Leu Leu Val Ser Asp Val Gly Thr Ile Val Trp Gly Ala
                130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
                180                 185                 190

Arg Ile Met Ala Trp Leu Phe Phe Leu Ser Trp Gly Met Phe Pro Val
                195                 200                 205

Leu Phe Val Val Gly Pro Glu Gly Phe Asp Ala Ile Ser Val Tyr Gly
                210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
                260                 265                 270

Glu Met Glu Val Glu Thr Met Val Asp Gln Glu Asp Glu Glu Thr Val
                275                 280                 285

<210> SEQ ID NO 4
<211> LENGTH: 288
<212> TYPE: PRT
<213> ORGANISM: Artificial Sequence
```

<220> FEATURE:
<223> OTHER INFORMATION: synthetic sequence

<400> SEQUENCE: 4

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30

Asn Ile Leu Gln Trp Phe Ala Phe Gly Phe Ser Ile Leu Ile Leu Met
        35                  40                  45

Phe Tyr Ala Tyr Gln Thr Trp Arg Ala Thr Cys Gly Trp Glu Glu Val
50                  55                  60

Tyr Val Cys Ser Ile Glu Leu Thr Lys Val Ile Glu Phe Phe His
65                  70                  75                  80

Glu Phe Asp Asp Pro Ser Met Leu Tyr Leu Ala Asn Gly His Arg Val
                85                  90                  95

Gln Trp Leu Arg Tyr Ala Glu Trp Leu Leu Thr Cys Pro Val Ile Leu
            100                 105                 110

Ile His Leu Ser Asn Leu Thr Gly Leu Lys Asp Asp Tyr Ser Lys Arg
        115                 120                 125

Thr Met Arg Leu Leu Val Ser Asp Val Gly Thr Ile Val Trp Gly Ala
130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
            260                 265                 270

Glu Met Glu Val Glu Thr Met Val Asp Gln Glu Asp Glu Thr Val
        275                 280                 285

<210> SEQ ID NO 5
<211> LENGTH: 288
<212> TYPE: PRT
<213> ORGANISM: Artificial Sequence
<220> FEATURE:
<223> OTHER INFORMATION: synthetic sequence

<400> SEQUENCE: 5

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30

Asn Ile Leu Gln Trp Phe Ala Phe Gly Phe Ser Ile Leu Ile Leu Met
        35                  40                  45

Phe Tyr Ala Tyr Gln Thr Trp Arg Ala Thr Cys Gly Trp Glu Glu Val

```
            50                  55                  60
Tyr Val Cys Cys Val Glu Leu Thr Lys Val Ile Ile Glu Phe Phe His
 65                  70                  75                  80

Glu Phe Asp Asp Pro Ser Met Leu Tyr Leu Ala Asn Gly His Arg Val
                 85                  90                  95

Gln Trp Leu Arg Tyr Ala Glu Trp Leu Leu Thr Cys Pro Val Ile Leu
            100                 105                 110

Ile His Leu Ser Asn Leu Thr Gly Leu Lys Asp Asp Tyr Ser Lys Arg
            115                 120                 125

Thr Met Arg Leu Leu Val Ser Asp Val Gly Cys Ile Val Trp Gly Ala
        130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
            260                 265                 270

Glu Met Glu Val Glu Thr Met Val Asp Gln Glu Asp Glu Thr Val
        275                 280                 285

<210> SEQ ID NO 6
<211> LENGTH: 288
<212> TYPE: PRT
<213> ORGANISM: Artificial Sequence
<220> FEATURE:
<223> OTHER INFORMATION: synthetic sequence

<400> SEQUENCE: 6

Met Leu Gly Asn Gly Ser Ala Ile Val Pro Ile Asp Gln Cys Phe Cys
 1               5                  10                  15

Leu Ala Trp Thr Asp Ser Leu Gly Ser Asp Thr Glu Gln Leu Val Ala
             20                  25                  30

Asn Ile Leu Gln Trp Phe Ala Phe Gly Phe Ser Ile Leu Ile Leu Met
         35                  40                  45

Phe Tyr Ala Tyr Gln Thr Trp Arg Ala Thr Cys Gly Trp Glu Glu Val
 50                  55                  60

Tyr Val Cys Cys Val Glu Leu Thr Lys Val Ile Ile Glu Phe Phe His
 65                  70                  75                  80

Glu Phe Asp Asp Pro Ser Met Leu Tyr Leu Ala Asn Gly His Arg Val
                 85                  90                  95

Gln Trp Leu Arg Tyr Ala Glu Trp Leu Leu Thr Cys Pro Val Ile Leu
            100                 105                 110

Ile His Leu Ser Asn Leu Thr Gly Leu Lys Asp Asp Tyr Ser Lys Arg
            115                 120                 125

Thr Met Arg Leu Leu Val Ser Asp Val Gly Thr Ile Val Trp Gly Ala
```

```
            130                 135                 140
Ala Ala Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
                180                 185                 190

Arg Ile Met Ala Trp Leu Phe Phe Leu Ser Trp Gly Met Phe Pro Val
                195                 200                 205

Leu Phe Val Val Gly Pro Glu Gly Phe Asp Ala Ile Ser Val Tyr Gly
210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
                260                 265                 270

Glu Met Glu Val Glu Thr Met Val Asp Gln Glu Asp Glu Glu Thr Val
                275                 280                 285

<210> SEQ ID NO 7
<211> LENGTH: 288
<212> TYPE: PRT
<213> ORGANISM: Artificial Sequence
<220> FEATURE:
<223> OTHER INFORMATION: synthetic sequence

<400> SEQUENCE: 7

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
                20                  25                  30

Asn Ile Leu Gln Trp Phe Ala Phe Gly Phe Ser Ile Leu Ile Leu Met
                35                  40                  45

Phe Tyr Ala Tyr Gln Thr Trp Arg Ala Thr Cys Gly Trp Glu Glu Val
50                  55                  60

Tyr Val Cys Thr Leu Glu Leu Thr Lys Val Ile Ile Glu Phe Phe His
65                  70                  75                  80

Glu Phe Asp Asp Pro Ser Met Leu Tyr Leu Ala Asn Gly His Arg Val
                85                  90                  95

Gln Trp Leu Arg Tyr Ala Glu Trp Leu Leu Thr Cys Pro Val Ile Leu
                100                 105                 110

Ile His Leu Ser Asn Leu Thr Gly Leu Lys Asp Asp Tyr Ser Lys Arg
                115                 120                 125

Thr Met Arg Leu Leu Val Ser Asp Val Gly Thr Ile Val Trp Gly Ala
                130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
                180                 185                 190

Arg Ile Met Ala Trp Leu Phe Phe Leu Ser Trp Gly Met Phe Pro Val
                195                 200                 205

Leu Phe Val Val Gly Pro Glu Gly Phe Asp Ala Ile Ser Val Tyr Gly
```

```
            210                 215                 220
Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
            260                 265                 270

Glu Met Glu Val Glu Thr Met Val Asp Gln Glu Asp Glu Glu Thr Val
            275                 280                 285

<210> SEQ ID NO 8
<211> LENGTH: 288
<212> TYPE: PRT
<213> ORGANISM: Artificial Sequence
<220> FEATURE:
<223> OTHER INFORMATION: synthetic sequence

<400> SEQUENCE: 8

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
                20                  25                  30

Asn Ile Leu Gln Trp Phe Ala Phe Gly Phe Ser Ile Leu Ile Leu Met
            35                  40                  45

Phe Tyr Ala Tyr Gln Thr Trp Arg Ala Thr Cys Gly Trp Glu Glu Val
    50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly His Arg Val
                85                  90                  95

Gln Trp Leu Arg Tyr Ala Glu Trp Leu Leu Thr Cys Pro Val Ile Cys
            100                 105                 110

Ile His Leu Ser Asn Leu Thr Gly Leu Lys Asp Asp Tyr Ser Lys Arg
        115                 120                 125

Thr Met Arg Leu Leu Val Ser Asp Val Gly Cys Ile Val Trp Gly Ala
130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
            260                 265                 270

Glu Met Glu Val Glu Thr Met Val Asp Gln Glu Asp Glu Glu Thr Val
            275                 280                 285
```

```
<210> SEQ ID NO 9
<211> LENGTH: 288
<212> TYPE: PRT
<213> ORGANISM: Artificial Sequence
<220> FEATURE:
<223> OTHER INFORMATION: synthetic sequence

<400> SEQUENCE: 9

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30

Asn Ile Leu Gln Trp Phe Ala Phe Gly Phe Ser Ile Leu Ile Leu Met
        35                  40                  45

Phe Tyr Ala Tyr Gln Thr Trp Arg Ala Thr Cys Gly Trp Glu Glu Val
    50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly Glu Arg Val
                85                  90                  95

Gln Trp Leu Arg Tyr Ala Glu Trp Leu Leu Thr Cys Pro Val Ile Cys
            100                 105                 110

Ile His Leu Ser Asn Leu Thr Gly Leu Lys Asp Asp Tyr Ser Lys Arg
        115                 120                 125

Thr Met Arg Leu Leu Val Ser Asp Val Gly Thr Ile Val Trp Gly Ala
    130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
    210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
            260                 265                 270

Glu Met Glu Val Glu Thr Met Val Asp Gln Glu Asp Glu Glu Thr Val
        275                 280                 285

<210> SEQ ID NO 10
<211> LENGTH: 288
<212> TYPE: PRT
<213> ORGANISM: Artificial Sequence
<220> FEATURE:
<223> OTHER INFORMATION: synthetic sequence

<400> SEQUENCE: 10

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30
```

```
Asn Ile Leu Gln Trp Phe Ala Phe Gly Phe Ser Ile Leu Ile Leu Met
        35                  40                  45

Phe Tyr Ala Tyr Gln Thr Trp Arg Ala Thr Cys Gly Trp Glu Glu Val
    50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly Glu Arg Val
                85                  90                  95

Gln Trp Leu Arg Tyr Ala Glu Trp Leu Leu Thr Cys Pro Val Ile Cys
            100                 105                 110

Ile His Leu Ser Asn Leu Thr Gly Leu Lys Asp Asp Tyr Ser Lys Arg
        115                 120                 125

Thr Met Arg Leu Leu Val Ser Asp Val Gly Thr Ile Val Trp Gly Ala
    130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
    210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Thr Thr Lys Ile Asn Val Ala Gly Glu
            260                 265                 270

Glu Met Glu Val Glu Thr Met Val Asp Gln Glu Asp Glu Glu Thr Val
        275                 280                 285
```

UNITED STATES PATENT AND TRADEMARK OFFICE
CERTIFICATE OF CORRECTION

PATENT NO. : 12,234,267 B2
APPLICATION NO. : 17/324501
DATED : February 25, 2025
INVENTOR(S) : Pan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 733 days.

Signed and Sealed this
Second Day of September, 2025

Coke Morgan Stewart
*Acting Director of the United States Patent and Trademark Office*